(12) United States Patent
Tachibana et al.

(10) Patent No.: US 9,593,331 B2
(45) Date of Patent: Mar. 14, 2017

(54) DOUBLE-STRANDED NUCLEIC ACID MOLECULE FOR GENE EXPRESSION CONTROL

(71) Applicants: Akira Tachibana, Osaka (JP); Toshizumi Tanabe, Osaka (JP)

(72) Inventors: Akira Tachibana, Osaka (JP); Toshizumi Tanabe, Osaka (JP)

(73) Assignee: Osaka City University, Osaka (JP)

( * ) Notice: Subject to any disclaimer, the term of this patent is extended or adjusted under 35 U.S.C. 154(b) by 47 days.

(21) Appl. No.: 14/355,711

(22) PCT Filed: Nov. 1, 2012

(86) PCT No.: PCT/JP2012/078348
§ 371 (c)(1),
(2) Date: Jul. 11, 2014

(87) PCT Pub. No.: WO2013/065791
PCT Pub. Date: May 10, 2013

(65) Prior Publication Data
US 2014/0315982 A1    Oct. 23, 2014

(30) Foreign Application Priority Data
Nov. 2, 2011 (JP) .................... 2011-241547

(51) Int. Cl.
*C12N 15/11*    (2006.01)
*C12N 15/113*   (2010.01)
*A61K 31/7105*  (2006.01)

(52) U.S. Cl.
CPC ........ *C12N 15/113* (2013.01); *A61K 31/7105* (2013.01); *C12N 15/111* (2013.01); *C12N 2310/11* (2013.01); *C12N 2310/14* (2013.01); *C12N 2310/531* (2013.01); *C12N 2320/50* (2013.01); *C12N 2320/51* (2013.01)

(58) Field of Classification Search
CPC .. C12N 15/113; C12N 15/111; C12N 2310/11
See application file for complete search history.

(56) References Cited

U.S. PATENT DOCUMENTS

| 8,815,821 B2 * | 8/2014 | Woolf ................ | A61K 31/713 514/44 A |
| 2007/0149470 A1 | 6/2007 | Kaspar et al. | |
| 2008/0171715 A1 * | 7/2008 | Brown ................ | C12N 15/111 514/44 A |
| 2008/0318887 A1 * | 12/2008 | Trent ................ | A61K 31/711 514/44 R |
| 2010/0286378 A1 | 11/2010 | Li et al. | |
| 2011/0217769 A1 * | 9/2011 | Rossi ................ | C12N 15/1132 435/325 |
| 2011/0306653 A1 | 12/2011 | Hirao et al. | |
| 2012/0022138 A1 * | 1/2012 | Santel ................ | C12N 15/111 514/44 A |

FOREIGN PATENT DOCUMENTS

| EP | 1849865 A1 | 10/2007 |
| EP | 2562257 A1 | 2/2013 |
| JP | 2008-512500 A | 4/2008 |
| JP | 2010-537640 A | 12/2010 |
| WO | WO 2005/078089 A1 | 8/2005 |
| WO | WO 2006/031901 A2 | 3/2006 |
| WO | WO2010/032704 A1 * | 3/2010 |
| WO | WO 2011/075188 A1 | 6/2011 |
| WO | WO 2011/132672 A1 | 10/2011 |

OTHER PUBLICATIONS

English translation of WO 2010/032704A1 from the WIPO Gold Translate Web Tool, pp. 1-35, translated on Sep. 9, 2015.*
Supplementary European Search Report dated Apr. 22, 2015, in EP 12846621.6.
Ando et al., "Two-step cleavage of hairpin RNA with 5' overhangs by human DICER," BMC Molecular Biology, Feb. 9, 2011, 12(1):1-12 and "Supplementary material," Feb. 9, 2011, XP002738354, http://www.biomedcentral.com/content/supplementary/1471-2199-12-6-sl.pdf (retrieved on Apr. 14, 2015), 6 pages.
Bramsen et al., "Improved silencing properties using small internally segmented interfering RNAs," Nucleic Acids Research, 2007, 35(17):5886-5897.
Elbashir et al., "Functional anatomy of siRNAs for mediating efficient RNAi in Drosophila melanogaster embryo lysate," The EMBO Journal, 2001, 20(23):6877-6888.
Ghildiyal et al., "Small silencing RNAs: an expanding universe," Nature Reviews Genetics, 2009, 10:94-108.
Henn et al., "Inhibition of Dicing of Guanosine-Rich shRNAs by Quadruplex-Binding Compounds," ChemBioChem, 2008, 9:2722-2729.
Ida et al., "DNA Chikangata miRNA Sa n miRNA Kassei eno Eikyo," Dai 83 Kai Annual Meeting of the JapaneseBiochemical Society Dai 33 Kai Annual Meeting of the Molecular Biological Society of Japan Godo Taikai Koen Yoshishu, 2010, 4P-0803, with English translation.
Ida et al., "Altered miRNA Strands Affected the Activity of miRNA," Annual Meeting of the Molecular Biology Society of Japan Program Yoshishu, Nov. 21, 2011, 4T10p1-6(4P-0141), with English translation.
Mook et al., "Evaluation of locked nucleic acid-modified small interfering RNA in vitro and in vivo," Mol. Cancer Ther., Mar. 2007, 6(3):833-843.
Sun et al., "Asymmetric RNA duplexes mediate RNA interference in mammalian cells," Nature Biotechnology, Dec. 2008, 26(12):1379-1382.

* cited by examiner

Primary Examiner — Brian Whiteman
(74) Attorney, Agent, or Firm — Foley & Lardner LLP

(57) ABSTRACT

Provided are an improved double-stranded nucleic acid molecule involved in gene expression control mediated by a gene silencing mechanism, a method of producing the molecule, and a pharmaceutical composition comprising the double-stranded nucleic acid molecule. The double-stranded nucleic acid molecule for gene expression control comprises an antisense strand having a length of 18 to 28 nucleotides and a sense strand including a complementary moiety composed of a sequence sufficiently complementary to the antisense strand and a protruding single-stranded 5'-end moiety having a length of 2 to 100 nucleotides. The sense strand and the antisense strand form base pairs via the complementary moiety. The method produces such a double-stranded nucleic acid molecule, and the pharmaceutical composition contains such a double-stranded nucleic acid molecule as an active ingredient.

19 Claims, 22 Drawing Sheets

Fig. 4
A
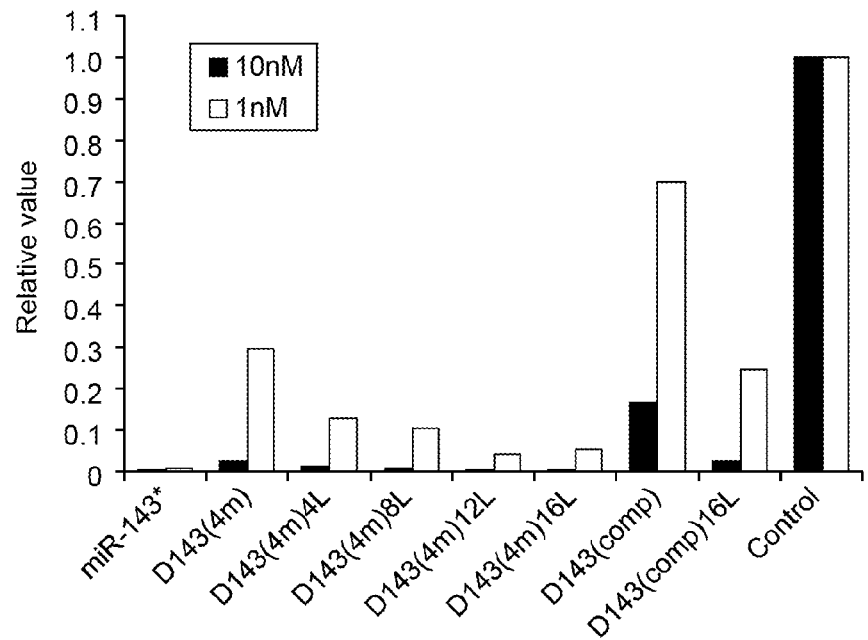
B
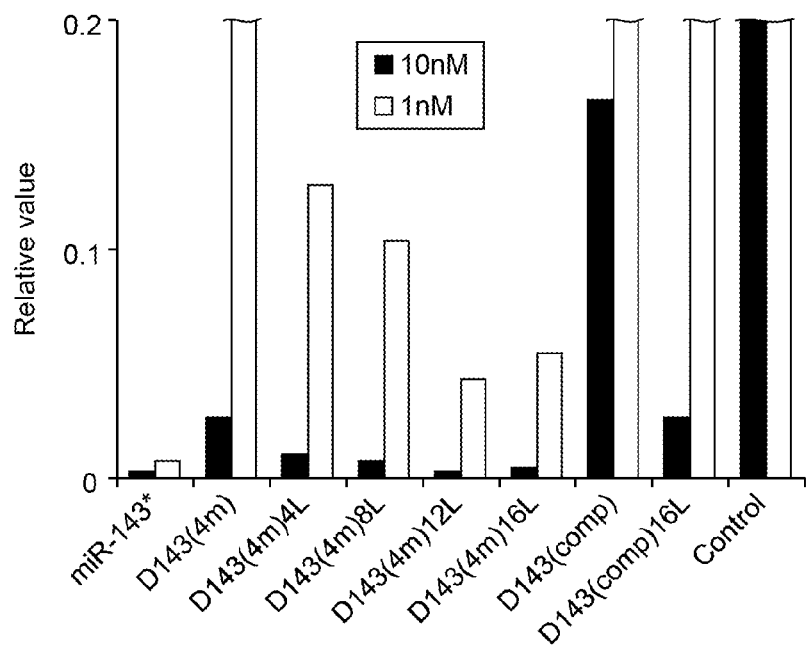

Fig. 8

```
outGinG:   GCGTATTTC GAGAGGGAG -5'
           A ||||||||  ||||||||
           AGCATAAAAG AGGAGAGAG CAACGTCGAGGAAGGTGACTGCCAA-3'   (SEQ ID NO:62)
                                |||||||||||||||||||||||||
           siPolR2A-AS: 3'--guugcaacucccuuccacugacgguu-5'      (SEQ ID NO:2)

outGinA:   GCGTATTTC GAGAGGGAG -5'
           A ||||||||  ||||||||
           AGCATAAAAGACACAAAACA CAACGTCGAGGAAGGTGACTGCCAA-3'   (SEQ ID NO:63)
                                |||||||||||||||||||||||||
           siPolR2A-AS: 3'--guugcaacucccuuccacugacgguu-5'      (SEQ ID NO:2)

outAinG:   GCGTATTTCACAAAACACA -5'
           A ||||||||
           AGCATAAAAG AGGAGAGAG CAACGTCGAGGAAGGTGACTGCCAA-3'   (SEQ ID NO:64)
                                |||||||||||||||||||||||||
           siPolR2A-AS: 3'--guugcaacucccuuccacugacgguu-5'      (SEQ ID NO:2)

outAinA:   GCGTATTTCACAAAACACA -5'
           A ||||||||||||||||||
           AGCATAAAAGACACAAAACACAACGTCGAGGAAGGTGACTGCCAA-3'   (SEQ ID NO:65)
                                |||||||||||||||||||||||||
           siPolR2A-AS: 3'--guugcaacucccuuccacugacgguu-5'      (SEQ ID NO:2)
```

Fig. 11 double G:
```
  GG TCATGAGGGGG ATCAT-5'
       ||||||||||||||||
G GGGGG TAGTATCAACGTCGAGGAAGGTGACTGCCAA-3'  (SEQ ID NO:69)
        ||||||||||||||||||||||||||||||
siPolR2A-AS: 3'--guugcaacucccuuccacugacgguu-5'  (SEQ ID NO:2)
``` center G:
```
  ATTCATGAGGGGG ATCAT-5'
       ||||||||||||||||
T ATAGTACT GGGGG TAGTATCAACGTCGAGGAAGGTGACTGCCAA-3'  (SEQ ID NO:70)
            ||||||||||||||||||||||||||||||
siPolR2A-AS: 3'--guugcaacucccuuccacugacgguu-5'  (SEQ ID NO:2)
``` outside G:
```
  GGGGC TCATGAAT-5'
       ||||||||
G GGGGA GTACTTATCAACGTCGAGGAAGGTGACTGCCAA-3'  (SEQ ID NO:71)
        ||||||||||||||||||||||||||||||
siPolR2A-AS: 3'--guugcaacucccuuccacugacgguu-5'  (SEQ ID NO:2)
```

Fig. 15
A
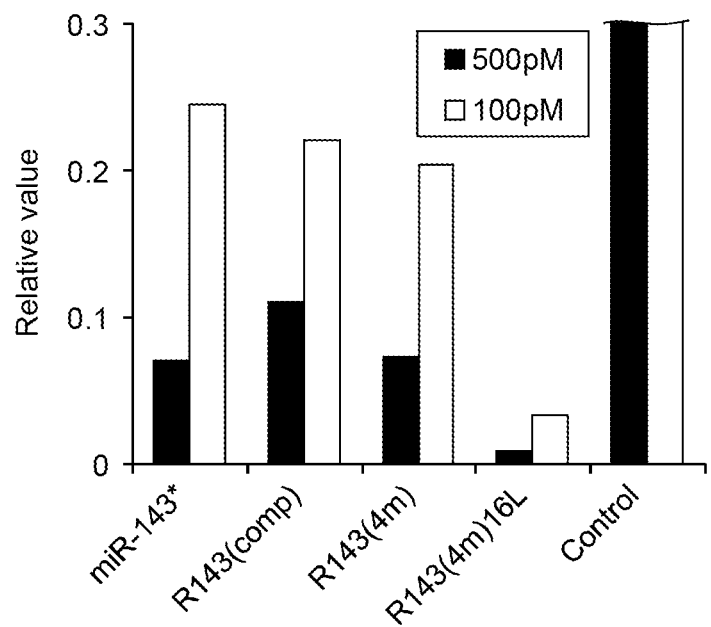
B
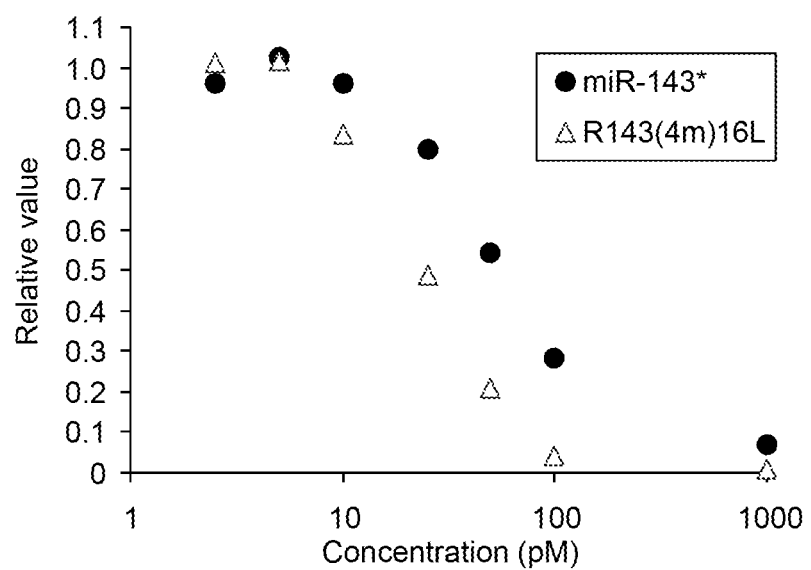

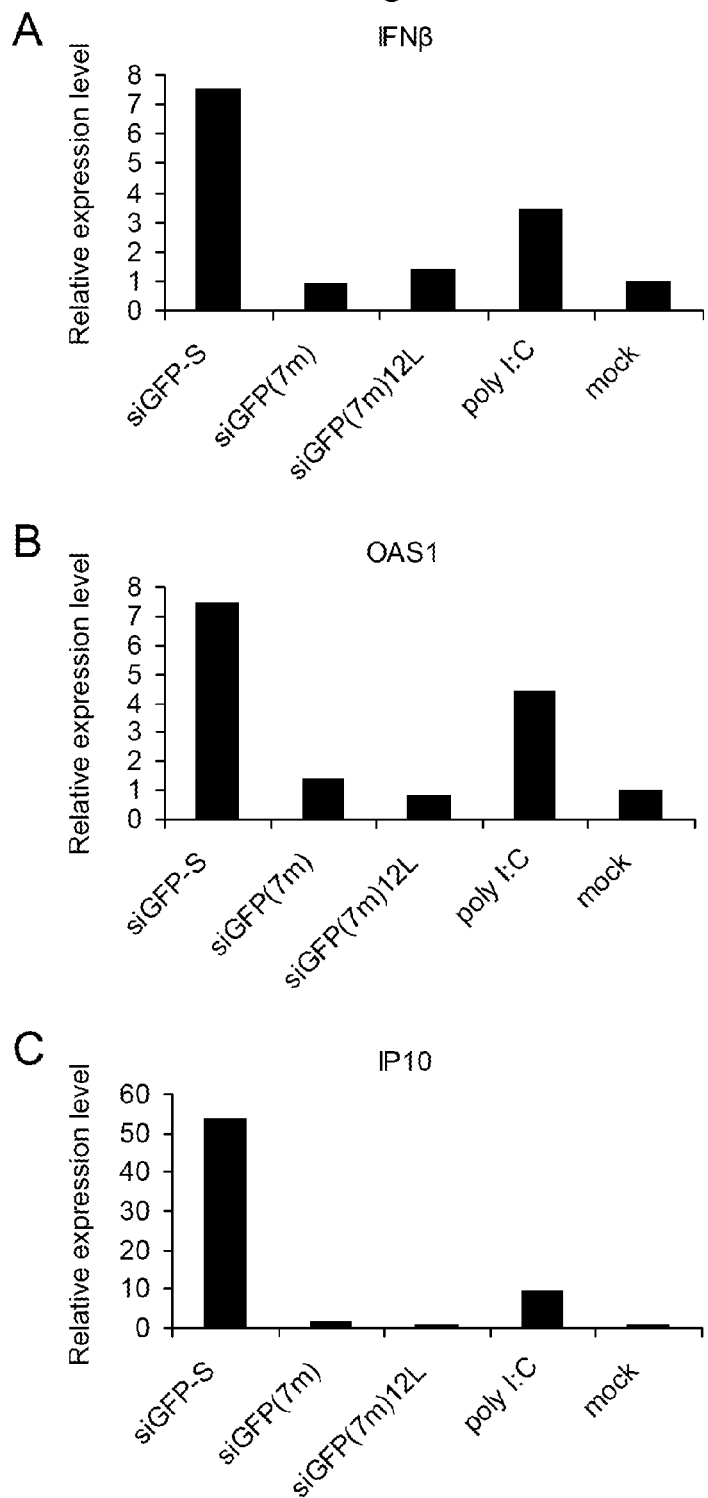

DOUBLE-STRANDED NUCLEIC ACID MOLECULE FOR GENE EXPRESSION CONTROL

CROSS-REFERENCE TO RELATED APPLICATIONS

This application is a National Stage application of PCT/JP2012/078348, filed Nov. 1, 2012, which claims priority from Japanese application JP 2011-241547, filed Nov. 2, 2011.

The instant application contains a Sequence Listing which has been submitted in ASCII format via EFS-WEB and is hereby incorporated by reference in its entirety. Said ASCII copy, created on Mar. 21, 2016, is named sequence.txt and is 19 KB.

TECHNICAL FIELD

The present invention relates to an improved double-stranded nucleic acid molecule involved in gene expression control mediated by a gene silencing mechanism and a method of producing the same. The invention also relates to a pharmaceutical composition comprising such a double-stranded nucleic acid molecule.

BACKGROUND ART

A mechanism of controlling gene expression mediated by a small RNA having a length of about 20 to 30 nucleotides is called gene silencing. This mechanism is widely reserved in a variety of biological species from yeast to human and has been revealed to be involved in regulation of many important vital phenomena such as development, metabolism, and virus infection control. In addition, at present, RNA interference (RNAi) method, which inhibits gene expression through a gene silencing mechanism using small RNA, has been establishing a position as an indispensable gene functional analysis tool in the biological research field. Furthermore, such small RNA shows the effect of suppressing the expression of, for example, a gene or virus in vivo and is therefore expected as a next-generation nucleic acid drug.

One example of the small RNA mediating gene silencing is a small interfering RNA (siRNA), which is generated by Dicer enzyme processing of, for example, a foreign long double-stranded RNA or an RNA with a hairpin structure. One strand (called antisense strand) of the generated double-stranded siRNA is incorporated into a complex, called RNA-induced silencing complex (RISC), binds to a target mRNA having a complementary sequence, and induces cleavage of the target mRNA to sequence-specifically suppress expression of the gene. Meanwhile, a group of functional small RNAs, called microRNAs (miRNAs), is present in a cell. The miRNA is an endogenous small RNA that is natively expressed in the cell and is believed to suppress expression of another gene. The miRNA is generated by Drosha and then Dicer enzyme processing of a long miRNA precursor having a hairpin structure. It is believed that one strand of the generated double-stranded miRNA is, as in the case of a siRNA, incorporated into an RISC and then binds to an mRNA having a 3'-untranslated region including a sequence partially complementary to the miRNA to inhibit translation into a protein (see Non Patent Literature 1 for the review).

The small double-stranded RNA that mediates gene silencing is generated by a Dicer enzyme, as described above, and therefore has a constant structure, i.e., being composed of two RNAs each consisting of about 21 to about 24 nucleotides and forms a double-stranded RNA having an overhang of two nucleotides at the 3'-end of each strand. Accordingly, many of the siRNAs that are generally used in the present RNAi method are chemically synthesized products having an overhang of two nucleotides at each 3'-end. There have been some studies on the correlation between the structure and the activity of such siRNAs. For example, Elbashir et al. tested the activities of siRNA molecules each having a length of 21 nucleotides and having overhangs of various lengths at the 3'- or 5'-ends and confirmed that an overhang of two nucleotides at a 3'-end shows the highest efficiency (Non Patent Literature 2). In addition, they have reported that although the RNAi activity disappears by completely replacing one strand or both strands of the siRNA with 2'-deoxyribonucleotides, similar replacement of only the 3'-overhang of two nucleotides does not affect the RNAi activity (Non Patent Literature 2). Sun et al. showed that an asymmetric double-stranded RNA (aiRNA) of which the sense strand is shorter than a typical siRNA with a length of 21 nucleotides has an effective RNAi activity and reduces the off-target effect of the sense strand (Non Patent Literature 3). Bramsen et al. showed a design of a novel siRNA (sisiRNA) composed of an intact antisense strand and two short (a length of 10 to 12 nucleotides) sense strands (Non Patent Literature 4). The sisiRNA has been reported to have an activity equivalent to that of usual siRNA and to be low in off-target effect. These siRNA molecules having novel structures may have modifications, such as locked nucleic acid (LNA), and are further expensive than usual expensive RNAs having high synthetic cost by its nature. Thus, they have difficulty in practical use. Furthermore, the effect of controlling gene expression of siRNA varies considerably depending on the sequence design, and the effect is insufficient in many cases. In such a case, an increase in dose of the siRNA is required, which leads to a disadvantage that a risk of undesirable effects such as an off-target effect is raised.

CITATION LIST

Non Patent Literature

Non Patent Literature 1: Ghildiyal M. and Zamore P. D., 2009, Nat. Rev. Genet., 10, 94-108
Non Patent Literature 2: Elbashir et al., 2001, EMBO J., 20, 6877-6888
Non Patent Literature 3: Sun et al., 2008, Nat. Biotechnol., 26, 1379-1382
Non Patent Literature 4: Bramsen et al., 2007, Nucleic Acid Res., 35, 5886-5897

SUMMARY OF INVENTION

Technical Problem

It is an object of the present invention to provide a double-stranded nucleic acid molecule that has a high gene expression-suppressing activity and mediates gene silencing mechanism.

Solution to Problem

The present inventors have diligently studied to solve the above-mentioned problems and, as a result, have found that a double-stranded nucleic acid molecule including a sense strand having a moiety complementary to the antisense strand and a protruding moiety at the 5'-end has a high gene expression-suppressing activity, and have accomplished the present invention.

That is, the present invention encompasses the following inventions.

[1] A double-stranded nucleic acid molecule for gene expression control, comprising:
an antisense strand having a length of 18 to 28 nucleotides; and
a sense strand including a complementary moiety composed of a sequence sufficiently complementary to the antisense strand and a protruding single-stranded 5'-end moiety having a length of 2 to 100 nucleotides, wherein
the sense strand and the antisense strand form base pairs via the complementary moiety.

[2] The double-stranded nucleic acid molecule according to [1], wherein the antisense strand is composed of ribonucleotides.

[3] The double-stranded nucleic acid molecule according to [1] or [2], wherein the antisense strand is a miRNA.

[4] The double-stranded nucleic acid molecule according to any one of [1] to [3], wherein the antisense strand is composed of a sequence sufficiently complementary to a target sequence of a target gene.

[5] The double-stranded nucleic acid molecule according to any of [1] to [4], wherein the complementary moiety included in the sense strand is composed of ribonucleotides.

[6] The double-stranded nucleic acid molecule according to any of [1] to [5], wherein the sense strand is composed of ribonucleotides.

[7] The double-stranded nucleic acid molecule according to any of [1] to [4], wherein the sense strand is composed of deoxyribonucleotides.

[8] The double-stranded nucleic acid molecule according to any of [1] to [7], wherein the protruding single-stranded moiety has a G content of 30% to 80% based on the length of the protruding single-stranded moiety.

[9] The double-stranded nucleic acid molecule according to any of [1] to [8], wherein the protruding single-stranded moiety comprises one or more G-rich regions.

[10] The double-stranded nucleic acid molecule according to any of [1] to [9], wherein the protruding single-stranded moiety forms a double strand, a triplex, or a quadruplex.

[11] The double-stranded nucleic acid molecule according to any of [1] to [10], wherein the complementary moiety included in the sense strand has 0 to 30% of nucleotide mismatches with the antisense strand.

[12] A method of producing a double-stranded nucleic acid molecule according to any of [1] to [11], comprising the steps of:
(a) designing an antisense strand comprising a sequence sufficiently complementary to a target sequence of a target gene or selecting a miRNA as an antisense strand;
(b) designing a sense strand including a complementary moiety composed of a sequence sufficiently complementary to the antisense strand and a protruding single-stranded 5'-end moiety;
(c) synthesizing the antisense strand and the sense strand; and
(d) forming base pairs between the synthesized antisense strand and the sense strand.

[13] A pharmaceutical composition comprising a double-stranded nucleic acid molecule according to any of [1] to [11] as an active ingredient.

[14] The pharmaceutical composition according to [13], comprising a pharmaceutically acceptable carrier.

[15] A method of controlling gene expression in a cell, tissue, or individual, the method comprising the step of:
introducing a double-stranded nucleic acid molecule according to any of [1] to [11] into the cell, tissue, or individual.

The present specification encompasses the contents in the specification and/or drawings of Japanese Patent Application No. 2011-241547 based on which the present application claims priority.

Advantageous Effects of Invention

The double-stranded nucleic acid molecule of the present invention can effectively control gene expression.

BRIEF DESCRIPTION OF DRAWINGS

FIG. 4 shows graphs showing the gene expression-suppressing activity of an RNA antisense strand (miR-143) in cases of using DNA strands having protruding moietys of various nucleotide lengths as the sense strands. (B) is a graph obtained by magnifying the vertical axis of graph (A). The concentrations shown in the graphs are those of the double-stranded nucleic acid molecule used in transfection. The same shall apply hereinafter.

FIG. 8 shows the names, structures, nucleotide sequences, and SEQ ID NOs of molecules used in Example 1. DNAs are given in capital letters, and RNAs are given in small letters. The sequence regions surrounded by frames are G-rich regions.

FIG. 11 shows the names, structures, nucleotide sequences, and SEQ ID NOs of molecules used in Example 1. DNAs are given in capital letters, and RNAs are given in small letters. The sequence regions surrounded by frames are G-rich regions.

FIG. 15 shows (A) the gene expression-suppressing activity of an RNA antisense strand (miR-143) in cases of using RNA strands including various 5'-protruding moietys as the sense strands and (B) the gene expression-suppressing activity at low concentrations.

FIG. 22 shows innate immune responsiveness in human HeLa-S3 cells, wherein graphs A to C show the qRT-PCR results of IFNβ, OAS1, and IP10 mRNAs, respectively.

DESCRIPTION OF EMBODIMENTS

Figure 1:
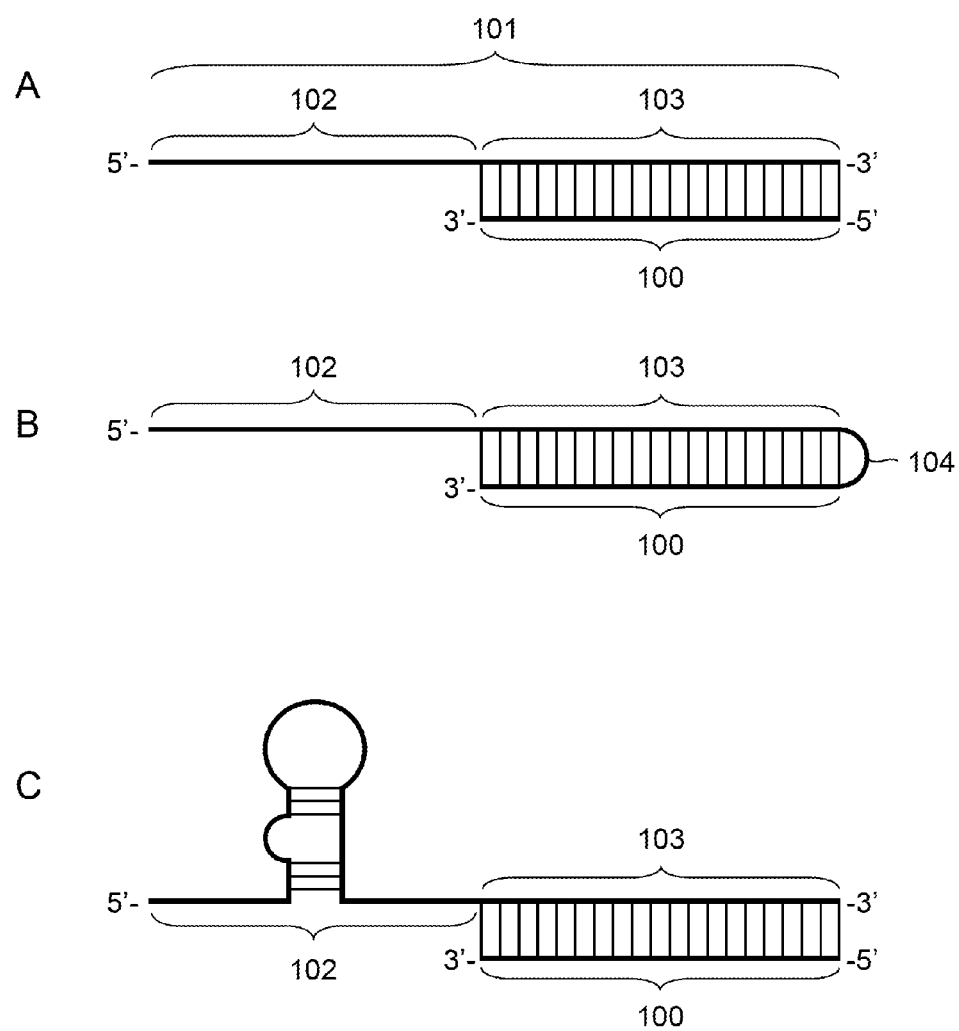
FIG. 1 shows conceptual diagrams illustrating the constitutions of double-stranded nucleic acid molecules according to the present invention. Diagram (A) shows a typical constitution composed of one antisense strand (100) and one sense strand (101), wherein the sense strand is composed of a protruding single-stranded moiety (102) at the 5'-side and a complementary moiety (103) to the antisense strand; diagram (B) shows a constitution composed of a sense strand and an antisense strand linked to each other with a spacer sequence (104); and diagram (C) shows a constitution having a double strand structure formed in the protruding single-stranded moiety.

The present invention will now be described in detail.
1. Double-Stranded Nucleic Acid Molecule
1-1. Summary A first aspect of the present invention relates to a double-stranded nucleic acid molecule for gene expression control. The double-stranded nucleic acid molecule of the present invention comprises an antisense strand and a sense strand including a complementary moiety composed of a sequence sufficiently complementary to the antisense strand and a protruding single-stranded 5'-end moiety.
1-2. Definition Throughout the present specification, the term "nucleic acid" refers to a natural nucleic acid, non-natural nucleic acid, and/or nucleic acid analog.

Throughout the present specification, the term "natural nucleic acid" refers to a naturally present biological macromolecule, of which the structural unit is nucleotides linked to one another by phosphodiester bonds. Usually, the natural nucleic acid is an RNA in which ribonucleotides each having any one of bases of adenine, guanine, cytosine, and uracil are linked or a DNA in which deoxyribonucleotides each having any one of bases of adenine, guanine, cytosine, and thymine are linked.

Throughout the present specification, the team "non-natural nucleic acid" refers to a nucleic acid including or composed of non-natural nucleotides. Herein, the term "non-natural nucleotide" refers to an artificially constructed or artificially chemically modified nucleotide that is not naturally present and is a nucleotide having a property and/or structure similar to that of the naturally present nucleotide or refers to a nucleotide including a nucleoside or a base having a property and/or structure similar to that of a naturally present nucleoside or base. Examples of the nucleoside include abasic nucleosides, arabinonucleosides, 2'-deoxyuridine, α-deoxyribonucleoside, β-L-deoxyribonucleoside, and other glycosylated nucleosides and further include nucleosides glycosylated with a substituted pentose (2'-O-methylribose. 2'-deoxy-2'-fluororibose, 3'-O-methylribose, or 1',2'-deoxyribose), arabinose, a substituted arabinose, a substituted hexose, or alpha anomer. In addition, the non-natural nucleotide includes an artificially constructed base analog or an artificially chemically modified base (modified base). Examples of the "base analog" include a 2-oxo(1H)-pyridin-3-yl group, a 5-position substituted 2-oxo(1H)-pyridin-3-yl group, a 2-amino-6-(2-thiazolyl)purin-9-yl group, a 2-amino-6-(2-thiazolyl)purin-9-yl group, and a 2-amino-6-(2-oxazolyl)purin-9-yl group. Examples of the "modified base" include modified pyrimidines (e.g., 5-hydroxycytosine, 5-fluorouracil, and 4-thiouracil), modified purines (e.g., 6-methyladenine and 6-thioguanosine), and other heterocyclic bases. The modified base may be a chemically modified nucleic acid such as methyl phosphonate DNA/RNA, phosphorothioate DNA/RNA, phosphoramidate DNA/RNA, or 2'-O-methyl DNA/RNA or a nucleic acid analog.

Throughout the present specification, the term "nucleic acid analog" refers to an artificially constructed compound having a structure and/or property similar to that of a natural nucleic acid. Examples of the nucleic acid analog include peptide nucleic acids (PNAs), peptide nucleic acids having phosphate groups (PHONAs), bridged nucleic acids/locked nucleic acids (BNAs/LNAs), and morpholino nucleic acids.

Furthermore, the phosphate group, sugar, and/or base of the nucleic acid of the present invention may be labeled with a nucleic acid-labeling material, as necessary. As the nucleic acid-labeling material, any material that is known in the art may be used, such as a radioisotope (e.g., $^{32}P$, $^{3}H$, or $^{14}C$), DIG, biotin, a fluorescent dye (e.g., FITC, Texas, cy3, cy5, cy7. FAM, HEX, VIC, JOE, Rox, TET, Bodipy493, NBD, or TAMRA), or a luminescent material (e.g., an acridinium ester).

Throughout the present specification, the term "double-stranded nucleic acid molecule" refers to two nucleic acid molecules forming base pairs between at least a part of the both nucleic acid molecules (see FIG. 1A), or a single nucleic acid molecule in which a double-stranded region is formed by base pairing, i.e., a hairpin-shaped nucleic acid molecule (see FIG. 1B). The single nucleic acid molecule is generally called a short hairpin RNA (shRNA).

Throughout the present specification, the term "complementary" refers to a relationship capable of forming a (e.g. Watson-Crick) base pair between two nucleotides, for example, the relationship between adenine and thymine or uracil and the relationship between cytosine and guanine. Throughout the present specification, the term "completely complementary" refers to that all of the successive nucleotides of a first nucleic acid sequence are complementary to the same number of successive nucleotides in a second nucleic acid sequence. Throughout the present specification, the term "sufficiently complementary" refers to that two nucleic acid sequences are not required to be completely complementary to each other and that one or both of the nucleic acid sequences have substitution, addition, and/or deletion of one or more nucleotides. Such substitution causes nucleotide mismatches, and the addition and deletion may cause unpaired nucleotides (bulge nucleotides).

Throughout the present specification, the term "gene silencing" (generally also called "RNA silencing") refers to a series of sequence-specific regulatory mechanism (for example, RNA interference (RNAi), transcriptional gene silencing (TGS), post-transcriptional gene silencing (PTGS), co-suppression, translational inhibition, or heterochromatin formation) causing inhibition or suppression of expression of a gene encoding a protein and generally mediated by RNA molecules. The gene silencing is observed in many organisms such as plants, animals, and fungi. For the gene silencing, please see, for example, Sharp P. A., 2001, Genes Dev., 15, 485-490: Zamore P. D., 2002, Science, 296, 1265-1269: Dernburg, A. F. and Karpen, G. H 2002, Cell, 111, 159-162; and Ghildiyal M. and Zamore P. D., 2009, Nat Rev Genet., 10, 94-108. In the present specification, suppression of the expression mediated by gene silencing during and/or after transcription of a gene is referred to as "gene expression control" or "controlling gene expression". Throughout the specification, these terms are used for suppression of the expression of a gene not only at a level of 100% but also at a level of 75% or more, 50% or more, or 20% or more, based on the expression level of mRNA or protein of the gene when the double-stranded nucleic acid molecule according to the present invention is not introduced. The degree of gene expression control can be determined by, for example, comparing the level of mRNA or protein of the gene in a cell or individual to which the double-stranded nucleic acid molecule of the present invention has been introduced with that in a cell or individual to which the double-stranded nucleic acid molecule of the present invention has not been introduced or another control double-stranded nucleic acid has been introduced. The mRNA level can be measured by, for example, Northern hybridization or RT-PCR. The protein level can be measured by Western blotting or ELISA or measuring protein activity or fluorescent intensity from fluorescent protein.

1-3. Constitution of Double-Stranded Nucleic Acid Molecule

The double-stranded nucleic acid molecule according to the present invention comprises an antisense strand and a sense strand described below. A typical schematic view thereof (a case of being composed of two nucleic acid molecules) is shown in FIG. 1A. The antisense strand in the present specification generally corresponds to the guide strand of a siRNA or the miRNA strand of a miRNA. The sense strand in the present specification corresponds to the passenger strand or the miRNA* (miRNA star) strand. The double-stranded nucleic acid molecule according to the present invention can suppress the expression of a specific gene during and/or after transcription by inducing gene silencing in a cell or a living body.

The term "antisense strand" refers to a nucleic acid molecule that has an ability of inducing above-described gene silencing and can suppress the expression of a specific gene. The antisense strand has a length of 18 to 28 nucleotides, preferably 20 to 25 nucleotides, more preferably 21 to 24 nucleotides, and particularly preferably 21 or 22 nucleotides.

In an embodiment, the antisense strand is a miRNA. The miRNA is an endogenous functional RNA encoded on the genome and having a length of about 21 to 24 nucleotides, and is believed to be involved in suppression of another gene. The miRNA sequence can be obtained from a known database such as miRbase (mirbase.org, Griffiths-Jones S., 2004, Nucleic Acid Res., 32, 109-111). Examples of natural miRNA include miR-143 (the sequence of human miR-143 is shown in SEQ ID NO: 1), miR-145, lin-4, let-7, miR-10, miR-15, miR-16, miR-168, miR-175, miR-196, and homologs thereof, and also include other natural miRNAs derived from model organisms such as a human, *Drosophila melanogaster, Caenorhabditis elegans, Danio rerio, Arabidopsis thaliana*, a mouse, and a rat.

In another embodiment, the antisense strand is a nucleic acid molecule comprising a sequence sufficiently complementary to the target sequence of a target gene. Such an antisense strand can be used for suppressing the expression of a target gene. The antisense strand can include 0 to 30%, 0 to 20%, or 0 to 10% of nucleotide mismatches with the target sequence of a target gene, based on the antisense strand length, but is not particularly limited thereto. The nucleotide mismatches may be appropriately determined within the range that the double-stranded nucleic acid molecule of the present invention including such an antisense strand can achieve suppression of the target gene expression. Specifically, the antisense strand may include 1 to 8, preferably 1 to 6, 1 to 4, 1 to 3, and particularly preferably 1 or 2 nucleotide mismatches with the target sequence of a target gene or may be completely complementary to the target sequence without nucleotide mismatches. For example, an antisense strand having a length of 21 nucleotides may include one, two, three, four, five, or six nucleotide mismatches with the target sequence of a target gene. Alternatively or additionally, the antisense strand may include one or two bulge nucleotides against the target sequence of a target gene.

Examples of the target gene in the present specification include, but not limited to, genes derived from organisms to which the double-stranded nucleic acid molecule of the present invention is introduced, genes of, for example, viruses, bacteria, and fungi present in the living bodies of infected living bodies, and artificially introduced genes (e.g., a gene present on a plasmid introduced into a cell by transfection). Examples of the genes derived from organisms include cancer genes, tumor suppressor genes, development-related genes, disease-related genes causing diseases, and genes essential for survival (e.g., RNA polymerase 2 A subunit genes). Furthermore, examples of the viruses and the bacteria include HIV, HBV, HCV, HTLV-1, HTLV-2, influenza virus, SARS coronavirus, norovirus, rotavirus, enterohemorrhagic *E. coli, Mycobacterium tuberculosis*, methicillin-resistant *staphylococcus aureus* (MRSA), *Pseudomonas aeruginosa, Streptococcus pyogenes, Candida*, and *Helicobacter pylori*. Examples of the artificially introduced genes include common reporter genes, for example, fluorescent protein genes, such as GFP and dsRed, luciferase genes, and 1 (GUS) genes.

Throughout the present specification, the term "target sequence" refers to specific successive sequences in, for example, the exon, intron, 5' and 3'-untranslated regions (UTRs), and controlling elements (e.g., promoter, enhancer, and silencer) of the target gene to be suppressed in expression by the double-stranded nucleic acid molecule of the present invention. The target sequence has a length of about 16 to about 30 nucleotides, such as 18 to 28 nucleotides, preferably 20 to 25 nucleotides, more preferably 21 to 24 nucleotides, and more preferably 21 or 22 nucleotides.

The "sense strand" used in the present invention is a nucleic acid molecule comprising a "complementary moiety" and a "protruding single-stranded moiety" described below. In the double-stranded nucleic acid molecule according to the present invention, the sense strand and the antisense strand form base pairs via the complementary moiety included in the sense strand.

The "complementary moiety" included in the sense strand refers to a moiety composed of a sequence sufficiently complementary to the antisense strand. The "complementary moiety" included in the sense strand can have 0 to 30%, 0 to 20%, or 0 to 10% of nucleotide mismatches with the antisense strand, based on the strand length of the "complementary moiety", but is not particularly limited thereto. The nucleotide mismatches may be appropriately determined within the range that the double-stranded nucleic acid molecule of the present invention including such a sense strand can achieve suppression of the target gene expression. Specifically, the "complementary moiety" included in the sense strand may include 1 to 8, preferably 1 to 6, 1 to 4, 1 to 3, and particularly preferably 1 or 2 nucleotide mismatches with the antisense strand or may be completely complementary to the antisense strand without nucleotide mismatches. For example, when the "complementary moiety" of a sense strand has a length of 21 nucleotides, the complementary moiety may include six, five, four, three, two, or one nucleotide mismatches with the antisense strand. Alternatively or additionally, the "complementary moiety" of a sense strand may include one or two bulge nucleotides with the antisense strand.

In general, the antisense strand is selected such that its complementation with a target sequence is high. The sense strand can be selected so as to include one or more mismatches with a sequence other than the target sequence in order to reduce an off-target effect, that is, to reduce the effect of inducing gene silencing by acting on a sequence other than the target sequence. Preferred number and positions of mismatches can be determined by measuring the gene expression-suppressing activity of the produced double-stranded nucleic acid molecule in accordance with, for example, the method described in an example described below.

Throughout the present specification, the term "protruding single-stranded moiety" or "protruding moiety" refers to a moiety adjacent to the 5'-side of the above-mentioned complementary moiety and not forming base pairs with the antisense strand present in a single-stranded form at the 5'-end of the sense strand when the sense strand and the antisense strand are allowed to form base pairs. This protruding moiety may have a length of 2 to 100 nucleotides, preferably 3 to 50 nucleotides, 4 to 45 nucleotides, 5 to 40 nucleotides, 5 to 35 nucleotides, 5 to 30 nucleotides 5 to 25 nucleotides, 6 to 24 nucleotides, 9 to 23 nucleotides, 11 to 22 nucleotides, 13 to 21 nucleotides, 15 to 20 nucleotides, or 16 to 19 nucleotides. The sequence of the protruding moiety can be arbitrarily set. A higher content of guanine (G) provides higher gene expression-suppressing activity and is therefore preferred. The G content of the protruding moiety is 0 to 100%, 0 to 80%, preferably 20 to 70%, more preferably 30 to 70%, 40 to 70%, 30 to 80%, 40 to 80%, 50 to 70%, or 50 to 80%, based on the length of the protruding moiety. A G content of 30% or more, in particular, 40% or more is defined as a high G content.

A protruding moiety having one or more G-rich regions also provides high gene expression-suppressing activity and is therefore preferred. The term "G-rich region" refers to successive sequences with a high G content in a protruding moiety or a region with a high G content formed by the conformation of a protruding moiety. The successive sequences with a high G content may have a length of 2 to 100 nucleotides, preferably 3 to 50 nucleotides, 4 to 50 nucleotides, 5 to 50 nucleotides, 5 to 25 nucleotides, or 10 to 20 nucleotides. The G content of the G-rich region can be 30 to 100%, preferably 40 to 100%, 50 to 100%, 60 to 100%, 70 to 100%, 80 to 100%, 90 to 100%, 50 to 90%, 60 to 90%, 70 to 90%, 80 to 90%, 50 to 80%, 60 to 80%, or 70 to 80%. The G-rich region can be a sequence including, for example, 5 to 10 successive guanine bases. The G-rich region may be present in any position in a protruding single-stranded moiety. For example, the G-rich region may be present in the 5'-end of a protruding single-stranded moiety, the inside of a protruding single-stranded moiety, or at the 3'-end of a protruding single-stranded moiety (i.e., adjacent to the complementary moiety of a sense strand).

The sense strand of the present invention includes the above-described complementary moiety and the protruding single-stranded moiety at the 5'-end and may further include any other arbitrary sequence as long as the double-stranded nucleic acid molecule of the present invention has the gene expression-suppressing activity. That is, the sense strand can include an arbitrary sequence having an arbitrary length at the 3'-end. In this case, the 3'-end of the sense strand is the protrusion end. Specifically, a 3'-protrusion end of one or two nucleotides (for example, UU or TT) is supposed. Alternatively, the 3'-end of a sense strand may be a blunt end or a recessed end having recess of one or two nucleotides. The 3'-end of a sense strand is preferably a blunt end.

In the double-stranded nucleic acid molecule according to the present invention, a part or the entire of the antisense strand and/or sense strand as the constituent may be a natural nucleic acid, non-natural nucleic acid, and/or nucleic acid analog. The non-natural nucleic acid and/or nucleic acid analog can be used for, for example, enhancing the stability of the nucleic acid molecule and/or reducing the off-target effect.

In the double-stranded nucleic acid molecule according to the present invention, the antisense strand is preferably composed of ribonucleotides. In an embodiment, the sense strand is composed of deoxyribonucleotides. In conventional technologies, the use of a DNA strand as a sense strand significantly decreases the gene expression-suppressing activity (Elbashir et al., 2001, EMBO J., 20, 6877-6888). However, the use of a sense strand having the structure of the present invention shows a high gene expression-suppressing activity, even if the sense strand is a DNA strand (see Example 1 below). In another embodiment, the sense strand is composed of ribonucleotides. In this case, significantly high gene expression-suppressing activity is observed. In Example 2 below, the detected activity was about 5 to 7 times higher than that in the case of using a natural double-stranded miRNA.

Embodiments in which the antisense strand, the sense strand, or the complementary moiety or protruding single-stranded moiety included in the sense strand is a chimeric strand of ribonucleotides and deoxyribonucleotides are also encompassed in the scope of the present invention. Specifically, the antisense strand, sense strand, above-mentioned complementary moiety, or protruding single-stranded moiety may be a chimeric strand composed of ribonucleotides, a part of which is substituted with deoxyribonucleotides. Reversely, the antisense strand, sense strand, above-mentioned complementary moiety, or protruding single-stranded moiety may be a chimeric strand composed of deoxyribonucleotides, a part of which is substituted with ribonucleotides. In a preferred embodiment of the present invention, the complementary moiety included in the sense strand is composed of ribonucleotides. In this case, the gene expression-suppressing activity was higher than that in the case of the complementary moiety composed of deoxyribonucleotides (see Example 3 below). In this case, the protruding single-stranded moiety included in the sense strand may be composed of deoxyribonucleotides or may be composed of ribonucleotides.

The constitution of the double-stranded nucleic acid molecule of the present invention will now be further described with reference to drawings. Typically, the double-stranded nucleic acid molecule of the present invention is composed of one antisense strand (100) and one sense strand (101) as shown in FIG. 1A. The sense strand is composed of a protruding single-stranded moiety (102) at the 5'-end and a complementary moiety (103) to the antisense strand.

The double-stranded nucleic acid molecule of the present invention may be in a hairpin shape as shown in FIG. 1B. In this case, the 5'-end of an antisense strand and the 3'-end of a sense strand are linked to each other via a spacer sequence (104). The spacer sequence can be an arbitrary nucleotide sequence that is usually composed of 3 to 24 nucleotides and preferably 4 to 15 nucleotides and does not cause self-base pairing. Accordingly, for example, when the complementary moiety included in the sense strand region and the antisense strand region each have a length of 21 nucleotides and when the protruding moiety is a hairpin-shaped double-stranded nucleic acid molecule having a length of 5 to 25 nucleotides, the total number of nucleotides of the entire molecule is 50 (21×2+5+3) to 91 (21×2+25+24). In such a hairpin-shaped double-stranded nucleic acid molecule, the complementary moiety included in the sense strand region and the antisense strand region form base pairs, and the spacer sequence positioned therebetween forms a loop structure. As a result, the entire molecule forms a hairpin-shaped stem-and-loop structure.

The double-stranded nucleic acid molecule of the present invention preferably forms a conformation with a part or the entire of the protruding single-stranded moiety. FIG. 1C is an example of a constitution having a double strand structure formed in a part of the protruding single-stranded moiety (102).

FIG. 2A is an example of a double-stranded nucleic acid molecule having a triplex structure formed in the protruding single-stranded moiety. The triplex structure is formed among three nucleic acid strands in the case when three nucleic acid strands include a specific nucleotide sequence. Examples of the "specific nucleotide sequence" include a sequence having successive guanine (G) and adenine (A) (GA sequence) and a sequence having successive thymine (T) and cytosine (C) (TC sequence). When two of the three nucleic acid strands include GA sequences and the remaining one sequence includes a CT sequence, base pairs are formed among three nucleotides, i.e., among GGC (the nucleotides are present, apart from each other, on the nucleotide sequence) and among AAT (same as above).

FIG. 2B shows an example of a double-stranded nucleic acid molecule having a quadruplex structure formed in the protruding single-stranded moiety. The quadruplex structure shown in this drawing is a structure (105) called G-quartet, where four Gs are arranged in a plane with hydrogen bonds, and two or more of such planes are formed so as to be stacked on each other. The G-quartet is formed in a single strand containing a G-rich nucleotide sequence, such as GGTTGGTGTGGTTGG (SEQ ID NO: 84), by intramolecular folding.

The present invention can provide a double-stranded nucleic acid molecule for gene expression control comprising an antisense strand having a length of 18 to 28 nucleotides and a sense strand including a complementary moiety composed of a sequence sufficiently complementary to the antisense strand and a protruding single-stranded 5'-end moiety having a length of 2 to 100 nucleotides, wherein the sense strand and the antisense strand form base pairs via the complementary moiety.

The present invention can also provide a gene expression inhibitor containing a double-stranded nucleic acid molecule comprising an antisense strand having a length of 18 to 28 nucleotides and a sense strand including a complementary moiety composed of a sequence sufficiently complementary to the antisense strand and a protruding single-stranded 5'-end moiety having a length of 2 to 100 nucleotides wherein the sense strand and the antisense strand form base pairs via the complementary moiety.

1-4. Producing Method

The above-mentioned double-stranded nucleic acid molecule can be easily designed and produced by those skilled in the art. Specifically, a method of producing the above-mentioned double-stranded nucleic acid molecule comprises the steps of:

(a) designing an antisense strand composed of a sequence sufficiently complementary to a target sequence of a target gene or selecting a miRNA as an antisense strand:

(b) designing a sense strand including a complementary moiety composed of a sequence sufficiently complementary to the antisense strand and a protruding single-stranded 5'-end moiety;

(c) synthesizing the antisense strand and the sense strand; and (d) forming base pairs between the synthesized antisense strand and sense strand.

In an embodiment of the step (a), an antisense strand composed of a sequence sufficiently complementary to the target sequence of a target gene is designed. In order to suppress the expression of only the target gene as far as possible, a specific region of the target gene is preferably selected as the target sequence. Herein, the term "specific region" refers to a region having a sequence that is not observed in other nucleic acid molecules in a cell in which suppression of target gene expression is performed. Accordingly, candidates are compared with appropriate genome databases of known organism species (e.g., a human, a mouse, and a rat), and every sequence significantly homologous to other sequences is excluded from the target sequence candidates. A method for sequence homology search is known as BLAST, which can be used on the National Center for Biotechnology Information website (ncbi.nlm.nih.gov). Subsequently, a sufficiently complementary sequence to the target sequence selected above is designed as an antisense strand. The details of the "sufficiently complementary sequence" in this case are the same as those described in "1-3. Constitution of double-stranded nucleic acid molecule", and the sequences are not required to be completely complementary to the target sequence and may contain, for example, one or more mismatches.

In another embodiment in the step (a), a miRNA is selected as the antisense strand of the double-stranded nucleic acid molecule. The sequence of the miRNA can be obtained from a known database such as miRbase (www.mirbase.org). Herein, the miRNA includes a homolog of a known miRNA.

In the step (b), the complementary moiety included in the sense strand including a sequence sufficiently complementary to the antisense strand is designed based on the sequence of the antisense strand designed or selected in the step (a). The details of the "sufficiently complementary sequence" in this case are the same as those described in "1-3. Constitution of double-stranded nucleic acid molecule", and the sequences are not required to be completely complementary to the antisense strand and may contain, for example, one or more mismatches. A protruding single-stranded 5'-end moiety is also designed at a position adjacent to the above-mentioned complementary moiety. The details of the protruding single-stranded moiety are referred to "1-3. Constitution of double-stranded nucleic acid molecule". The sense strand may be designed so as to include an appropriate sequence at the 3'-end as long as the double-stranded nucleic acid molecule of the present invention has a gene expression-suppressing activity.

In the step (c), the antisense strand and the sense strand designed or selected in the steps (a) and (b) can be enzymatically or chemically synthesized through manually or automatically operated reactions. These strands can be constituted from natural nucleic acids, non-natural nucleic acids, and/or nucleic acid analogs, as described above. The method of synthesizing an RNA or DNA molecule, in particular, chemical synthesis, is known in the field of the art (Verma S, and Eckstein F., 1998, Annul Rev. Biochem., 67, 99-134). Alternatively, an RNA molecule can also be prepared from a synthetic DNA template by in vitro transcription. Typically, an RNA is produced by transcription using a phage RNA polymerase, such as T7, T3, or SP6RNA polymerase, from a synthetic DNA template containing the sequence of an antisense strand or sense strand to be synthesized linked downstream of the promoter sequence (Milligan J. F. and Uhlenbeck O. C., 1989, Methods Enzymol., 180, 51-62). In preparation of a hairpin-shaped RNA by in vitro transcription, the RNA is produced by transcription from a DNA template in which a sense strand, a spacer sequence, and an antisense strand are linked, in the direction from the 5'-end to the 3'-end, to the downstream of the promoter sequence. An RNA or DNA molecule may be chemically synthesized by contract manufacturing services of a manufacturer (for example, Takara Bio Inc., Life Technologies, or Sigma-Aldrich Corporation). Each of the synthesized antisense strand and sense strand can be purified from a mixture by, for example, extraction with a solvent or resin, precipitation, electrophoresis, chromatography, or combination thereof. Alternatively, in order to avoid the loss of the product due to the treatment of the specimen, the product may not be purified or may be purified at a lowest degree.

In the step (d), the antisense strand and sense strand synthesized in the step (c) are mixed with each other in, for example, an appropriate annealing buffer (e.g., 100 mM KOAc, 2 mM MgOAc, 30 mM HEPES-KOH, pH 7.4) so as to give a concentration appropriate for the subsequent use (typically, the molar concentrations of the antisense strand and the sense strand are the same). The mixture is heated and is then gradually cooled to form base pairs. An example of the temperature conditions is at 95° C. for 3 min, then at 70° C. for 2 min, and then at 37° C. for 60 min. The produced double-stranded nucleic acid molecule may be purified as described above.

Alternatively, the double-stranded nucleic acid molecule of the present invention can be produced by introducing into a cell of interest a vector that expresses the double-stranded nucleic acid molecule of the present invention in a cell. In this case, two vectors that respectively express the sense strand and the antisense strand constituting a double-stranded nucleic acid molecule may be used, or a single vector including both a DNA fragment encoding the sense strand and a DNA fragment encoding the antisense strand of a double-stranded nucleic acid molecule may be used. Meanwhile, when a hairpin-shaped single-stranded molecule forms the double-stranded nucleic acid molecule, a vector containing a DNA fragment encoding the single-stranded molecule may be used.

The above-mentioned vector may be any vector that can express one of or both the strands of the double-stranded nucleic acid molecule of the present invention in a cell. The expression vector is not particularly limited, but is preferably a plasmid or virus. The vector may be appropriately selected depending on the host into which the vector is introduced. For example, when the host into which a vector is introduced is human, the vector can be a virus, such as adenovirus, retrovirus, or lentivirus, or vector based on a non-viral vector.

Such a vector can be easily constructed by those skilled in the art and can include a controlling element such as a promoter, enhancer, or terminator or a labeling region such as a selected marker gene, as necessary. Each of these elements is not particularly limited and may be appropriately selected from those known the field of the art depending on the host into which the expression vector is introduced.

The promoter can be any type that can function in a cell of interest. For example, a constitutive promoter or an inductive promoter may be used. Furthermore, the same promoter as that for suppressing the expression of a target gene can be used. In this case, for example, the transcriptional product of the target gene and the double-stranded nucleic acid molecule of the present invention for decomposing the transcriptional product can be simultaneously generated. In the case of inserting DNA fragments encoding the sense strand and the antisense strand into different two vectors separately, the same promoters or different promoters having equivalent expression activity are preferably used so that the expression levels of both strands are equivalent to each other.

1-5. Method of Use

The above-mentioned double-stranded nucleic acid molecule can be used in a method for controlling gene expression in a cell, tissue, or individual. The method comprises a step of introducing the double-stranded nucleic acid molecule produced as described above or a vector expressing the double-stranded nucleic acid molecule of the present invention into the cell, tissue, or individual.

The introduction of the double-stranded nucleic acid molecule of the present invention or a vector expressing the double-stranded nucleic acid molecule of the present invention is a method known in the field of the art and can be appropriately performed by those skilled in the art. Examples of physical methods include injection of a solution containing the molecule or vector, bombardment of particles coated with the molecule or vector, and electroporation in the presence of the molecule or vector. In addition, another method for introducing a nucleic acid into a cell, known in the field of the art, such as lipid-mediated carrier transport or chemical-mediated transport (e.g. calcium phosphate transfection), can be employed. The double-stranded nucleic acid molecule of the present invention or the vector may also be introduced together with components for an increase in uptake of the nucleic acid, acceleration of annealing of double strands, stabilization of annealed double strands, and/or acceleration of suppression of target gene expression.

The cell, tissue, or individual into which the double-stranded nucleic acid molecule or the vector of the present invention is introduced may be derived from any organism such as an animal and is preferably derived from a vertebrate animal. Examples of the vertebrate animal include, but not limited to, fishes and mammals such as bovines, goats, pigs, sheep, rodents (e.g., hamsters, mice, and rats), and primates (e.g., rhesus monkeys, chimpanzees, and humans).

The double-stranded nucleic acid molecule of the present invention can also be used as a reagent for research, for example, as a gene expression inhibitor or an RNAi reagent.

The double-stranded nucleic acid molecule of the present invention suppresses the expression of a specific gene in a cell, tissue, or individual according to the dose introduced thereinto. The nucleic acid molecule can be introduced in an amount that allows the delivery of at least one copy per cell. A high dose (for example, at least 5, 10, 100, 500, or 1000 copies per cell) of the nucleic acid molecule can more effectively suppress the expression.

1-6. Effect

The use of the double-stranded nucleic acid molecule according to the present invention induces gene silencing and can thereby sequence-specifically suppress gene expression in a cell, tissue, or individual. In particular, a sense strand composed of deoxyribonucleotides has a possibility of significantly high activity of controlling gene expression. In contrast, in conventional technologies, a sense strand composed of deoxyribonucleotides hardly shows the gene expression-suppressing activity. The double-stranded nucleic acid molecule of the present invention can significantly suppress gene expression. In addition, in this case, an advantage of considerably decreasing the manufacturing cost can be expected.

2. Pharmaceutical Composition Containing Double-Stranded Nucleic Acid Molecule of the Present Invention 2-1. Summary A second aspect of the present invention is a pharmaceutical composition containing the double-stranded nucleic acid molecule of the first aspect as an active ingredient. This composition can be used for preventing and/or treating a disease of a subject.

2-2. Constitution of Pharmaceutical Composition

In an embodiment, the antisense strand contained in the double-stranded nucleic acid molecule, which is an active ingredient of the pharmaceutical composition, of the present invention may be able to suppress the expression of a gene involving in a disease to be prevented and/or treated. Examples of the disease to be prevented and/or treated include cancers in which, for example, APC gene (colorectal cancer) or BRCA1/BRCA2 gene (breast cancer) is involved, neurodegenerative diseases in which, for example, PS1 gene (Alzheimer) is involved, and diseases in which, for example, LPL gene (hyperlipidemia) or INS/INSR gene (diabetes) is involved. Examples of the cancer to be prevented and/or treated include stomach cancer, esophageal cancer, colorectal cancer, hepatocellular carcinoma, pancreatic cancer, cholangiocarcinoma, breast cancer, lung cancer, lung adenocarcinoma, renal cancer, prostate cancer, bladder cancer, endometrial cancer, cervical cancer, thyroid cancer, ovarian cancer, skin cancer, leukemia, myeloma, lymphoma, and lymphosarcoma. For infectious diseases with viruses, bacteria, and so on, the double-stranded nucleic acid molecule of the present invention can be used for suppressing the expression of a viral gene or bacterial gene. Examples of the viruses and the bacteria include HIV, HBV, HCV, HTLV-1, HTLV-2, influenza virus, SARS coronavirus, norovirus, rotavirus, enterohemorrhagic *E. coli, Mycobacterium tuberculosis*, methicillin-resistant *staphylococcus aureus* (MRSA), *Pseudomonas aeruginosa, Streptococcus pyogens, Candida*, and *Helicobacter pylori*. Whole or partial genome sequences and genetic information thereof are known, and a target sequence can be selected based on the genomes and the genetic information. As a result, the antisense strand constituting the double-stranded nucleic acid molecule, which is an active ingredient of the pharmaceutical composition, of the present invention can be designed.

In another embodiment, a disease caused by abnormality in function or expression of an endogenous small RNA, such as a miRNA, is prevented and/or treated. In this case, for example, a natural miRNA can be used as the antisense strand constituting the double-stranded nucleic acid molecule, which is an active ingredient of the pharmaceutical composition, of the present invention.

In the pharmaceutical composition for preventing and/or treating a cancer, the antisense strand of the double-stranded nucleic acid molecule can be a cancer-inhibiting miRNA, such as miR-122, miR-223, miR-124, miR-194, miR-152, miR-16, miR-141, miR-143, miR-145, or miR-200c. The use of an antisense strand targeting a gene (e.g., RNA polymerase PolR2A) that is important in proliferation and/or survival of cells is preferred.

The pharmaceutical composition of the present invention contains a medium for the double-stranded nucleic acid molecule of the present invention as an active ingredient. Examples of the medium include water, ethanol, propylene glycol, ethoxylated isostearyl alcohol, polyoxylated isostearyl alcohol, and polyoxyethylene sorbitan fatty acid esters. These media are desirably sterilized and are preferably adjusted to be isotonic with blood as necessary.

The pharmaceutical composition of the present invention can further contain a pharmaceutically acceptable carrier as necessary. The term "pharmaceutically acceptable carrier" refers to an additive that is usually used in the pharmaceutical technical field. Examples of the carrier include excipients, binders, disintegrants, fillers, emulsifiers, fluidity additive modifiers, and lubricants.

Examples of the excipient include sugars such as monosaccharides, disaccharides, cyclodextrins, and polysaccharides (more specific non-limiting examples thereof include glucose, sucrose, lactose, raffinose, mannitol, sorbitol, inositol, dextrin, maltodextrin, starch, and cellulose), metal salts (e.g., sodium chloride, sodium phosphate or calcium phosphate, calcium sulfate, magnesium sulfate, and calcium carbonate), citric acid, tartaric acid, glycine, low-, medium-, and high-molecular weight polyethylene glycols (PEGs), Pluronic, kaolin, silicic acid, and combinations thereof Examples of the binder include starch pastes from corn, wheat, rice, or potato starch; simple syrup, glucose solution, gelatin, tragacanth, methylcellulose, hydroxypropyl methylcellulose, sodium carboxymethyl cellulose, shellac, and polyvinyl pyrrolidone.

Examples of the disintegrant include the starches, lactose, carboxymethyl starch, cross-linked polyvinyl pyrrolidone, agar, laminarin powder, sodium bicarbonate, calcium carbonate, alginic acid or sodium alginate, polyoxyethylene sorbitan fatty acid esters, sodium lauryl sulfate, stearic acid monoglyceride, and salts thereof.

Examples of the filler include the sugars and calcium phosphates (e.g., tricalcium phosphate and calcium hydrogen phosphate).

Examples of the emulsifier include sorbitan fatty acid esters, glycerin fatty acid esters, sucrose fatty acid esters, and propylene glycol fatty acid esters.

Examples of the fluidity additive modifier and lubricant include silicates, talc, stearates, and polyethylene glycol.

These carriers are mainly used for facilitating the formulation of the dosage form and maintaining the dosage form and pharmaceutical effects and may be appropriately used as necessary. If necessary, the composition may further contain a flavoring agent, a pH adjuster, a solubilizer, a suspending agent, a diluent, a surfactant, an extender, a stabilizer, an absorption promoter, a humidity agent, a moisturizing agent, an adsorbent, a disintegration inhibitor, a coating agent, a preservative, a coloring agent, an antioxidant, a flavor, a flavoring agent, a sweetener, and a buffer, in addition to the above-mentioned additives.

The pharmaceutical composition of the present invention can contain another drug within a range that does not impair the pharmacological effect of the double-stranded nucleic acid molecule. For example, in a case of an injection, the composition may contain a predetermined amount of an antibiotic. Furthermore, the composition can also contain another drug effective for delivering the double-stranded nucleic acid molecule to a target tissue and/or a target cell.

Furthermore, the pharmaceutical composition of the embodiment can be in a combination formulation by containing another active ingredient within a range that is pharmaceutically acceptable and does not inactivate the double-stranded nucleic acid molecule of the present invention.

The pharmaceutical composition of the embodiment is not particularly limited, as long as it has a dosage form that does not inactivate the double-stranded nucleic acid molecule as an active ingredient and another additional active ingredient, and may be, for example, a liquid, solid, or semisolid. Specific examples of the dosage form include parenteral dosage forms such as injections, suspensions, emulsions, ophthalmic solutions, creams, nasal drops, ointments, plasters, fomentations, and suppositories; and oral dosage forms such as liquids, powders, tablets, granules, capsules, sublingual formulations, and troches. The dosage form is preferably an injection.

2-3. Route of Administration

The pharmaceutical composition of the embodiment can be administered to a living body in a pharmaceutically effective amount for treating a disease of interest. The living body to which the composition is administered is a vertebrate animal, preferably a mammal such as a human.

Throughout the present specification, the term "pharmaceutically effective amount" refers to a dose necessary for that the double-stranded nucleic acid molecule contained in the pharmaceutical composition of the present invention prevents or treats a disease as an object or relieves a symptom of the disease (e.g., a dose capable of suppressing the expression of a gene causing the disease) and hardly or does not cause harmful side effects (e.g., off-target effect or innate immune response) to the living body to which the composition is administered. The double-stranded nucleic acid molecule of the present invention of which the antisense strand is composed of ribonucleotides has a higher gene expression-suppressing activity compared to siRNA molecules having general structures and therefore has an advantage that the amount contained in the pharmaceutical composition can be reduced. In addition, the double-stranded nucleic acid molecule of the present invention of which the antisense strand is composed of deoxyribonucleotides has a possibility of being more stable against nuclease compared to RNA strands and therefore has a possibility of decreasing the dose. The specific dose varies depending on the type of the causative gene for the disease to be prevented and/or treated, the mechanism of action for onset of the gene, the gene expression-suppressing activity and stability of the double-stranded nucleic acid molecule according to the present invention, the dosage form used, the information of a subject, and the administration route. In the case of administration to a human, the range of the pharmaceutically effective amount and a preferred administration route are decided based on data obtained by general cell culture assay and animal experiments. The ultimate dose for individual subject is determined by, for example, doctor's judgment and is adjusted. On this occasion, the information of the subject to be considered includes the progress or severity of the disease, systemic conditions of the subject's health, age, weight, sex, dietary habit, drug sensitivity, and tolerance to the therapy.

The administration of the double-stranded nucleic acid molecule of the present invention may be systemic administration or topical administration, which can be appropriately selected depending on, for example, the type of a disease, the site of onset, or the progress of the disease. When the site of disease onset is local, direct topical administration by, for example, injection to the onset site and the circumference thereof is preferred. Such administration allows a sufficient amount of the double-stranded nucleic acid molecule of the present invention to be administered to the site (tissue or organ) to be treated and also hardly affects other tissues. In contrast, in the cases of being incapable of specifying the site of the treated area, as in metastatic cancer, or of systemic onset of a disease, systemic administration, for example, intravenous injection is preferred, but not limited thereto. Such administration allows the double-stranded nucleic acid molecule of the present invention to be distributed via the blood flow throughout the body, resulting in a possibility of administration to a lesion area that cannot be found by diagnosis.

The double-stranded nucleic acid molecule of the present invention can be administered by any proper method that does not inactivate the contained active ingredient. For example, the administration may be parenteral (e.g., injection, aerosol, application, instillation, or rhinenchysis) or oral and is preferably injection.

In administration by injection, the injection site is not particularly limited, as long as the double-stranded nucleic acid molecule of the present invention exert its function and can achieve the purpose of the pharmaceutical composition.

Examples of the injection site include veins, arteries, the liver, muscles, joints, the marrow, the medullary cavity, the ventricles, transcutaneous sites, subcutaneous sites, intracutaneous sites, the abdominal cavity, the nasal cavity, the bowels, and sublingual sites. Preferred examples are injection into blood vessels, such as intravenous injection and intraarterial injection. Such administration, as described above, allows the pharmaceutical composition of the present invention to be distributed via the blood flow throughout the body and is relatively low in invasiveness.

2-4. Effects

The pharmaceutical composition containing the double-stranded nucleic acid molecule of the present invention as an active ingredient is effective as a low-dose and low-cost gene expression inhibitor, is expected to suppress expression of various genes by appropriately designing the sequence of the antisense strand, and can be applied to prophylaxis and/or therapy of a variety of diseases. Furthermore, although usual siRNAs are known to cause innate immune response by recognition of a double-stranded RNA, the double-stranded nucleic acid molecule of the present invention hardly causes such a side effect and thereby can provide a highly safe pharmaceutical composition.

EXAMPLES

The present invention will now be more specifically described by examples. However, the technical scope of the present invention is not limited to the following examples.
(Synthetic Oligonucleotide)

The sequences of the oligonucleotides used in the following examples are shown in Tables 1-1, 1-2, 2-1, 2-2, and 3. Antisense strands are shown in the 3' to 5' direction from left to right, and sense strands are shown in the 5' to 3' direction from left to right (the nucleotides are positioned such that both strands form base pairs). Capital letters denote deoxyribonucleotides, and small letters denote ribonucleotides. Italic bold letters denote protruding single-stranded moietys included in sense strands, and underlined bold letters denote nucleotide mismatches on sense strands with antisense strands.

TABLE 1-1

Oligonucleotides used in examples shown in FIGS. 3, 4, 15 to 19, and 21

| | FIG. | Name | Sequence | SEQ ID NO: |
|---|---|---|---|---|
| Antisense (3' to 5') | 3,4, 15-19,21 | miR-143 | cucgaugucacgaaguagagu | 1 |
| Sense (5' to 3') | 3,4, 15-19,21 | miR-143' | ggugcagugcugccaucucuggu | 10 |
| | 3 | D143(4m) | GAGGTACAGTGCTTCATCTCA | 11 |
| | | D143(4m)16L | *GCGTAGGCGTTGGAGC*GAGGTACAGTGCTTCATCTCA | 12 |
| | 4 | D143(4m) | GAGGTACAGTGCTTCATCTCA | 11 |
| | | D143(4m)4L | *GAGC*GAGGTACAGTGCTTCATCTCA | 13 |
| | | D143(4m)8L | *GTTGGAGC*GAGGTACAGTGCTTCATCTCA | 14 |
| | | D143(4m)12L | *AGGCGTTGGAGC*GAGGTACAGTGCTTCATCTCA | 15 |
| | | D143(4m)16L | *GCGTAGGCGTTGGAGC*GAGGTACAGTGCTTCATCTCA | 12 |
| | | D143(comp) | GAGCTACAGTGCTTCATCTCA | 16 |
| | | D143(comp)16L | *GCGTAGGCGTTGGAGC*GAGCTACAGTGCTTCATCTCA | 17 |
| | 15 | R143(comp) | gagcuacagugcuucaucuca | 45 |
| | | R143(4m) | gagguacagugcuucaucuca | 46 |
| | | R143(4m)16L | *gcguaggcguuggagc*gagguacagugcuucaucuca | 47 |
| | 16 | R143(4m) | gagguacagugcuucaucuca | 46 |
| | | R143(4m)9L | *cguuggagc*gagguacagugcuucaucuca | 48 |
| | | R143(4m)10L | *gcguuggagc*gagguacagugcuucaucuca | 49 |
| | | R143(4m)11L | *ggcguuggagc*gagguacagugcuucaucuca | 50 |
| | | R143(4m)12L | *aggcguuggagc*gagguacagugcuucaucuca | 51 |
| | | R143(4m)13L | *uaggcguuggagc*gagguacagugcuucaucuca | 52 |
| | | R143(4m)14L | *guaggcguuggagc*gagguacagugcuucaucuca | 53 |
| | | R143(4m)15L | *cguaggcguuggagc*gagguacagugcuucaucuca | 54 |
| | | R143(4m)16L | *gcguaggcguuggagc*gagguacagugcuucaucuca | 47 |
| | | R143(4m)18L | *gggcguaggcguuggagc*gagguacagugcuucaucuca | 55 |
| | | R143(4m)20L | *gagggcguaggcguuggagc*gagguacagugcuucaucuca | 56 |
| | | R143(4m)24L | *gagagagggcguaggcguuggagc*gagguacagugcuucaucuca | 57 |
| | 17 | R143(4m) | gagguacagugcuucaucuca | 46 |
| | | R143(4m)9L | *cguuggagc*gagguacagugcuucaucuca | 48 |
| | | R143(4m)16L | *gcguaggcguuggagc*gagguacagugcuucaucuca | 47 |

TABLE 1-2

| | Figure | Name | Sequence | SEQ ID NO: |
|---|---|---|---|---|
| Sense (5' to 3') | 18 | D143(4m) | GAGGTACAGTGCTTCATCTCA | 11 |
| | | D143(4m)16L | *GCGTAGGCGTTGGAGC*GAGGTACAGTGCTTCATCTCA | 12 |
| | | D143(4m)R16L | *gcguaggcguuggagc*GAGGTACAGTGCTTCATCTCA | 58 |
| | | R143(4m) | gagguacagugcuucaucuca | 46 |
| | | R143(4m)16L | *gcguaggcguuggagc*gagguacagugcuucaucuca | 47 |
| | | R143(4m)D16L | *GCGTAGGCGTTGGAGC*gagguacagugcuucaucuca | 59 |
| | 19 | D143(4m) | GAGGTACAGTGCTTCATCTCA | 11 |
| | | D143(4m)3'16L | GAGGTACAGTGCTTCATCTCA*GCGTAGGCGTTGGAGC* | 60 |
| | | R143(4m) | gagguacagugcuucaucuca | 46 |
| | | R143(4m)3'9L | gagguacagugcuucaucuca*cguuggagc* | 61 |
| | 21 | R143(4m)D16L | *GCGTAGGCGTTGGAGC*gagguacagugcuucaucuca | 59 |

In the sequences, DNAs are given in capital letters, and RNAs are given in small letters.

The first letters "D" and "R" of the sense strand names denote that the sense strands are DNA strands and RNA strands, respectively. In chimera sense strands (SEQ ID NOs: 58 and 59) of DNAs and RNAs, the first letters "D" and "R" denote that the complementary portions to antisense strands are DNA strands and RNA strands, respectively. "4 m" denotes that the fourth nucleotide from the 5'-end of the complementary portion is a nucleotide mismatch (given in an underlined bold letter) with the antisense strand.

"comp" denotes that the complementary portion is completely complementary to the antisense strand.

The last letters such as "4L" and "8L" of the sense strand names denote the nucleotide lengths of the 5'-protruding portions (given in italic bold letters) (The adjacent letters "D" and "R" denote that the protruding portions are DNAs and RNAs, respectively. "3" denotes that the protruding portion is present on the 3-end instead of the 5-end.)

TABLE 2-1

Oligonucleotides used in examples shown in FIGS. 5 to 7, 10, 13, 14, and 20

| | Figure | Name | Sequence | G-content (%) | SEQ ID NO: |
|---|---|---|---|---|---|
| Antisense (3' to 5') | 5-7,10,13, 14,20 | siPoIR2A-AS | guugcaacuccuuccacugacgguu | — | 2 |
| Sense (5' to 3') | 5-7,10,13, 14,20 | siPoIR2A-S | caacguugaggaaggugacugccaa | — | 18 |
| | 5 | 7m | CAACGTC̲GAGGAAGGTGACTGCCAA | — | 19 |
| | | T3 | *TTT*CAACGTC̲GAGGAAGGTGACTGCCAA | 0 | 20 |
| | | T6 | *TTTTTT*CAACGTC̲GAGGAAGGTGACTGCCAA | 0 | 21 |
| | | T9 | *TTTTTTTTT*CAACGTC̲GAGGAAGGTGACTGCCAA | 0 | 22 |
| | | T12 | *TTTTTTTTTTTT*CAACGTC̲GAGGAAGGTGACTGCCAA | 0 | 23 |
| | | T15 | *TTTTTTTTTTTTTTT*CAACGTC̲GAGGAAGGTGACTGCCAA | 0 | 24 |
| | | 1 | *CCTGAAGTTCATCTGCA*CAACGTC̲GAGGAAGGTGACTGCCAA | 18 | 25 |
| | | 2 | *TTGAAGTCCCAGTCGAA*CAACGTC̲GAGGAAGGTGACTGCCAA | 24 | 26 |
| | | 3 | *ACCCTGAAGTTCATCTGCA*CAACGTC̲GAGGAAGGTGACTGCCAA | 16 | 27 |
| | | 4 | *AAGCTGACCCTGAAGTTC*CAACGTC̲GAGGAAGGTGACTGCCAA | 22 | 28 |
| | | 5 | *AAGCTGACCCTGAAGTTCATCTGCA*CAACGTC̲GAGGAAGGTGACTGCCAA | 20 | 29 |
| | | 6 | *TGTGGTAGTTGGAGC*CAACGTC̲GAGGAAGGTGACTGCCAA | 47 | 30 |
| | | 7 | *GCGTAGGCAAGAGTG*CAACGTC̲GAGGAAGGTGACTGCCAA | 47 | 31 |
| | 6 | 7m | CAACGTC̲GAGGAAGGTGACTGCCAA | — | 19 |
| | | AAGG-6 | *AAGAAG*CAACGTC̲GAGGAAGGTGACTGCCAA | 33 | 32 |
| | | AAC-6 | *AACAAC*CAACGTC̲GAGGAAGGTGACTGCCAA | 0 | 33 |
| | | CCA-6 | *CCACCA*CAACGTC̲GAGGAAGGTGACTGCCAA | 0 | 34 |
| | | CCT-6 | *CCTCCT*CAACGTC̲GAGGAAGGTGACTGCCAA | 0 | 35 |
| | | TTG-6 | *TTGTTG*CAACGTC̲GAGGAAGGTGACTGCCAA | 33 | 36 |
| | | TTC-6 | *TTCTTC*CAACGTC̲GAGGAAGGTGACTGCCAA | 0 | 37 |
| | | GGA-6 | *GGAGGA*CAACGTC̲GAGGAAGGTGACTGCCAA | 67 | 38 |
| | | GGT-6 | *GGTGGT*CAACGTC̲GAGGAAGGTGACTGCCAA | 67 | 39 |
| | 7 | 7m | CAACGTC̲GAGGAAGGTGACTGCCAA | — | 19 |
| | | GGA-6 | *GGAGGA*CAACGTC̲GAGGAAGGTGACTGCCAA | 67 | 38 |
| | | GGA-9 | *GAGGGAGAG*CAACGTC̲GAGGAAGGTGACTGCCAA | 67 | 40 |
| | | GGA-12 | *GGAGAGGGAGAG*CAACGTC̲GAGGAAGGTGACTGCCAA | 67 | 41 |
| | | GGA-15 | *GAGGGAGAGGGAGAG*CAACGTC̲GAGGAAGGTGACTGCCAA | 67 | 42 |
| | | GGA-18 | *GGAGAGGGAGAGGGAGAG*CAACGTC̲GAGGAAGGTGACTGCCAA | 67 | 43 |
| | | GGA-21 | *GAGGGAGAGGGAGAGGGAGAG*CAACGTC̲GAGGAAGGTGACTGCCAA | 67 | 44 |

TABLE 2-2

| | Figure | Name | Sequence | SEQ ID NO |
|---|---|---|---|---|
| Sense (5' to 3') | 10 | 7m | CAACGTCGAGGAAGGTGACTGCCAA | 19 |
| | | G15 | *GGGGAGGTGGGAGAG*CAACGTCGAGGAAGGTGACTGCCAA | 66 |
| | | G30 | *GGGGAGGTGGGAGAGGAGGGAGAGGGAGAG*CAACGTCGAGGAAGGTGACTGCCAA | 67 |
| | | G15_T15 | *GGGGAGGTGGGAGAGTATTTATATTTATAT*CAACGTCGAGGAAGGTGACTGCCAA | 68 |
| | 13 | 7m | CAACGTCGAGGAAGGTGACTGCCAA | 19 |
| | | G15 | *GGGGAGGTGGGAGAG*CAACGTCGAGGAAGGTGACTGCCAA | 66 |
| | | Gq2 | *GGTTGGTGTGGTTGG*CAACGTCGAGGAAGGTGACTGCCAA | 72 |
| | | Gq3 | *GGGTTGGGTGTGGGTTGGG*CAACGTCGAGGAAGGTGACTGCCAA | 73 |
| | | Gq4 | *GGGGTTGGGGTGTGGGGTTGGGG*CAACGTCGAGGAAGGTGACTGCCAA | 74 |
| | | Gq5 | *GGGGGTTGGGGGTGTGGGGGTTGGGGG*CAACGTCGAGGAAGGTGACTGCCAA | 75 |
| | 14 | 7m | CAACGTCGAGGAAGGTGACTGCCAA | 19 |
| | | Gq3 | *GGGTTGGGTGTGGGTTGGG*CAACGTCGAGGAAGGTGACTGCCAA | 73 |
| | | Gq3(3) | *GGGTTGGGTGTGGGTTGGGTTT*CAACGTCGAGGAAGGTGACTGCCAA | 76 |
| | | Gq3(6) | *GGGTTGGGTGTGGGTTGGGTTTTTT*CAACGTCGAGGAAGGTGACTGCCAA | 77 |
| | | Gq3(9) | *GGGTTGGGTGTGGGTTGGGTTTTTTTTT*CAACGTCGAGGAAGGTGACTGCCAA | 78 |
| | 20 | gga-5 | *ggaga*caacgucgaggaaggugacugccaa | 79 |

In the sequences, DNAs are given in capital letters, and RNAs are given in small letters. Protruding portions are given in italic bold letters, and nucleotide mismatches with antisense strands are given in underlined bold letters. "G-content (%)" denotes the guanine content based on the length of a single-stranded portion (given in italic bold letters).

TABLE 3

Oligonucleotides used in an examples shown in FIG. 22

| | Name | Sequence | SEQ ID NO: |
|---|---|---|---|
| Antisense (3' to 5') | siGFP-AS | gguguacuucgucgugcugaagaag | 80 |
| Sense (5' to 3') | siGFP-S | ccacaugaagcagcacgacuucuuc | 81 |
| | siGFP(7m) | CCACATCAAGCAGCACGACTTCTTC | 82 |
| | siGFP(7m) 12L | *GGAGAGGGAGAG*CCACATCAAGCAGCACGACTTCTTC | 83 |

In the sequences, DNAs are given in capital letters, and RNAs are given in small letters. Protruding portions are given in italic bold letters Tables 1-1 and 1-2 show the sequences of oligonucleotides used in examples of which the results are shown in FIGS. 3, 4, 15 to 19, and 21. In these examples, the gene expression-suppressing activities by the double-stranded nucleic acid molecules were measured using miR-143 (SEQ ID NO: 1) as the RNA antisense strand and a DNA strand, an RNA strand, or a DNA/RNA chimeric strand shown in Tables 1-1 and 1-2 as the sense strand, respectively. Tables 2-1 and 2-2 show the sequences of oligonucleotides used in examples of which the results are shown in FIGS. 5 to 7, 10, 13, 14, and 20. In these examples, siPolR2A-AS (SEQ ID NO: 2) was used as the RNA antisense strand, and a DNA strand or an RNA strand shown in Tables 2-1 and 2-2 was used as the sense strand, respectively. Table 3 shows the sequences of oligonucleotides used in the example shown in FIG. 22. In this example, siGFP-AS (SEQ ID NO: 80) was used as the RNA antisense strand, and each oligonucleotides shown in Table 3 was used as the sense strands.

DNA oligonucleotides were synthesized by FASMAC Co., Ltd. under contract. RNA oligonucleotides were synthesized by FASMAC Co., Ltd. or Sigma-Aldrich Japan K.K. under contract. The oligonucleotides were each dissolved in D-PBS(−) (0.2 g/L KCl, 8 g/L NaCl, 0.2 g/L $KH_2PO_4$, and 1.15 g/L $Na_2HPO_4$). Each pair of an antisense strand and a sense strand for evaluating the gene expression-suppressing activity was mixed, heated to 90° C., and then gradually cooled for annealing.

(Plasmid)

The multi-cloning site (positions from 1288 to 1363) of pDsRed2-C1 (Clontech Laboratories, Inc., catalog No. 632407) was modified into 5'-AGATCTCGAGAAGCTTA-GATATCGTCGACCCGGGATCCACCGGATCTAGA-TAACT GA-3' (SEQ ID NO: 3) to produce pDsRed2ERVSMA. The genetic engineering for the production, for example, extraction and purification of plasmid DNA, preparation of competent cells, transformation of E. coli, DNA cloning, and ligase reaction, was performed in accordance with standard procedures (Sambrook J., Fritsh E. F., and Maniatis T., (1989), Molecular Cloning: a laboratory manual. Cold Spring Harbor Laboratory, Cold Spring Harbor, Now York). The sequence encodes an Arg-Ser-Arg-Glu-Ala-translation stop codon as the C-end of DsRed2 protein and has EcoRV site (GATATC) adjacent to the stop codon on the downstream side. A pDsRed2-miR143 target and a pDsRed2-siPoIR2A target were respectively producedby linking DNA strands, 5'-GTAGGAGCTACAGTGCT-GATCTCAGAGCTACAGTGCTTCATCTCAGAGCTA-CAG TGCTTCATCTA-3' (SEQ ID NO: 4)15'-TGAGAT-GAAGCACTGTAGCTCTGAGATGAAGCACTGTAGC-TCTGAGATGAAGCAC TGTAGCTCCTAC-3' (SEQ ID NO: 5) or 5'-GTAGCAACGTTGAGGAAGGTGACTGC-CAACAACGTTGAGGAAGGTGACTGCCAA CAACGT-TGAGGAAGGTGACTGCCAA-3' (SEQ ID NO: 6)/5'-TGAGATGAAGCACTGTAGCTCTGAGATGAAGCA-CTGTAGCTCTGAGATGAAGCAC GTCACCTTCCT-CAACGTTGCTAC-3' (SEQ ID NO: 7), prepared by annealing, to the blunt end of pDsRed2ERVSMA cleaved with EcoRV. These linked sequences were each designed to have three times repeating sequence completely complementary to miR-143 (SEQ ID NO: 1) or siPolR2A-AS (SEQ ID NO: 2).

In order to correct the difference in transfection efficiency, pCAGGS-AFP (Momose T. et al., 1999, Dev. Growth Differ, 41, 335-44), which expresses GFP regardless of the activity of the double-stranded nucleic acid molecule, was used.

(Method of Measuring Gene Expression-Suppressing Activity)

Unless otherwise specified, the gene expression-suppressing activity of a double-stranded nucleic acid molecule was measured as follows.

HEK293T cells (human embryonic kidney cell) were seeded in a 24-well plate at 60000 cells/well. After 24 hours, the cells were transfected with a predetermined amount of a double-stranded nucleic acid molecule, 50 ng of plasmid pCAGGS-AFP expressing GFP, and 50 ng of the pDsRed2-miR143 target (when the antisense strand of the double-stranded nucleic acid molecule was miR-143) or the pDsRed2-siPolR2A target (when the antisense strand of the double-stranded nucleic acid molecule was siPolR2A-AS), using Lipofectamine™ LTX (Invitrogen) in accordance with the protocol of Invitrogen. As a control, a control siRNA (5'-gcgcgcuuuguaggauucgTT-3' (SEQ ID NO: 8)/5'-cgaauc-cuacaaagccgcTT-3' (SEQ ID NO: 9), capital letters: deoxyribonucleotide, small letters: ribonucleotide) having an unrelated sequence was annealed, and transfection was performed at the same concentrations. After 48 hours, the cells were destroyed with a surfactant-containing buffer TBST (20 mM Tris. pH 7.4, 0.15 M NaCl, 0.05% Triton X-100), followed by centrifugation (13.000×g, 30 min). The fluorescence of the supernatant was measured with a fluorescent plate reader (Fluoroskan Ascent FL, Thermofisher Scientific). The measured excitation and fluorescence wavelengths were, respectively, 485 nm and 538 nm in GFP and 544 nm and 590 nm in DsRed2.

(Measurement Principle)

The pDsRed2-miR143 target and the pDsRed2-siPolR2A target each include a DsRed2 gene at the downstream of the CMV promoter. The 3'-untranslated region (3'-UTR) of this gene is designed to have three times repeating sequence completely complementary to the antisense strand contained in the double-stranded nucleic acid molecule as a target to be measured for its activity. The antisense strand induces gene silencing of DsRed2 having the target sequence at the 3'-UTR to significantly suppress the expression. The difference in transfection efficiency is corrected with the fluorescence from the GFP expression vector pCAGGS-AFP co-transfected the plasmid (GFP is expressed regardless of the activity of a double-stranded nucleic acid molecule). When the ratio, "DsRed2 fluorescence/GFP fluorescence", in the use of the control siRNA is defined as 1, if each double-stranded nucleic acid molecule has a gene expression-suppressing activity, the ratio, "DsRed2 fluorescence/GFP fluorescence", in the use of the double-stranded nucleic acid molecule is 1 or less. Although the ratio varies among experiments, typically, a ratio of 0.2 or less is recognized to have a sufficiently high gene expression-suppressing activity. This ratio was used as the normalized DsRed2/GFP ratio (relative value).

Example 1

Figure 3:
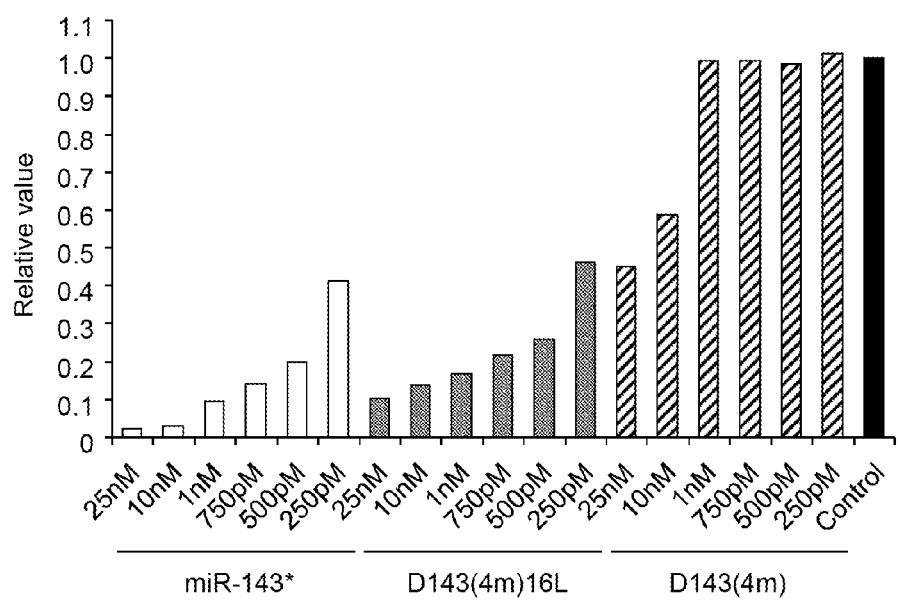
FIG. 3 is a graph showing the gene expression-suppressing activity of an RNA antisense strand (miR-143) in the case of using a natural miRNA* strand or a DNA strand as the sense strand. The sense strands contained in the used double-stranded nucleic acids are shown under the graph. The same shall apply hereinafter.

DNA Sense Strand Having 5'-Protruding Moiety (1) Gene Expression-Suppressing Activity in Use of DNA Sense Strand Having 5'-Protruding Moiety A gene expression-suppressing activity was confirmed using a double-stranded natural miRNA/miRNA* by the method of measuring activity described above. The use of miR-143 (SEQ ID NO: 1)/miR143* (SEQ ID NO: 10) (Table 1-1) decreased the normalized DsRed2/GFP ratio with an increase in concentration to show a concentration-dependent gene expression-suppressing activity (FIG. 3, miR-143).

Next, the gene expression-suppressing activity was evaluated with a DNA sense strand (Table 1-1. D143(4m), SEQ ID NO: 11) being sufficiently complementary to miR-143. Weak activities were observed at high concentrations (25 nM and 10 nM), but the activities were considerably low compared to natural m RNA/miRNA* (FIG. 3. D143(4m)).

Next, a DNA sense strand having a protruding moiety of 16 nucleotides at the 5'-end (Table 1-1, D143(4m) 16L, SEQ ID NO: 12) was used. Surprisingly, activities substantially equivalent to those in the use of natural miRNA* were detected over a broad concentration range (FIG. 3, D143(4m)16L). It has been reported that in conventional technologies, replacement of one strand of a double-stranded siRNA by a DNA strand causes a significant decrease in the activity (Elbashir et al., 2001, EMBO J. 20, 6877-6888). In contrast, the present inventors have first found that even if the whole sense strand is replaced by a DNA strand, a high gene expression-suppressing activity is maintained as long as the DNA has a 5'-protruding moiety.

(2) Investigation of Length and Sequence of Protruding Single-Stranded Moiety and Mismatch Between Antisense Strand and Sense Strand Various DNA sense strands were produced and were further evaluated for activities.

FIG. 4 shows the results in the use of miR-143 as the antisense strand as in above. DNA strands having one nucleotide mismatch and protruding moietys with various lengths were used as the DNA sense strands (Table 1-1, D143(4m), D143(4m)4L to D143(4m)16L: SEQ ID NO: 11 to 15). The results revealed that DNA sense strands having 5'-protruding moietys of various lengths all had high activities compared to that not having any protruding moiety (FIGS. 4A and 4B). It was suggested that DNA sense strands having a Si-protruding moiety with a length of 12 or 16 nucleotides have particularly high activities (FIG. 4B). The use of a DNA sense strand not having any mismatches (Table 1-1, D143(comp), SEQ ID NO: 16) had an activity lower than that having a mismatch (FIG. 4A comparison between D143(4m) and D143(comp)). However, even in a DNA sense strand not having any mismatches, the activity was increased by introducing a 5'-protruding moiety into the sense strand (FIG. 4A, comparison between D143(comp) and D143(comp)16L).

The results shown in FIG. 4 suggest that the 5'-protrusion and mismatch can synergistically contribute to an increase in gene expression-suppressing activity.

Figure 5:
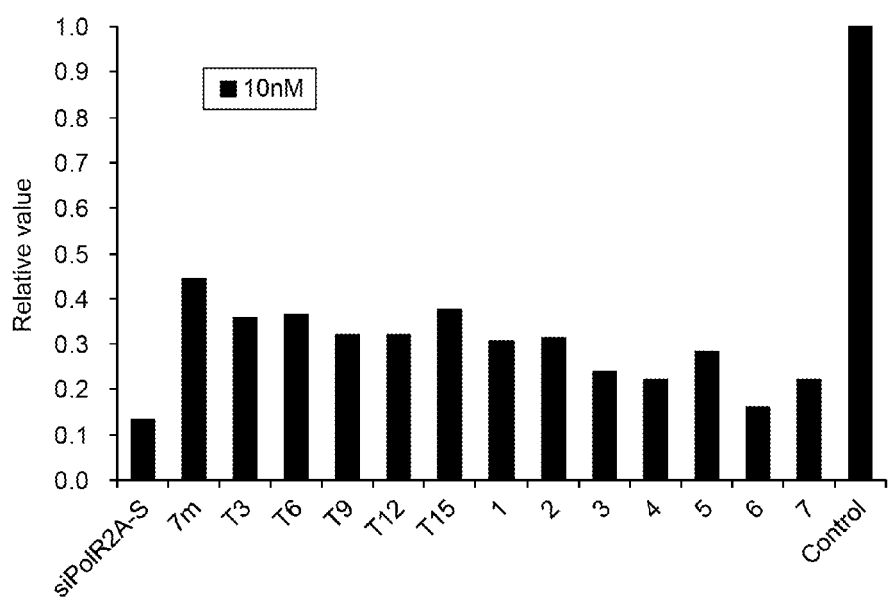
FIG. 5 shows the gene expression-suppressing activity of an RNA antisense strand (siPolR2A-AS) in cases of using DNA strands including 5'-protruding moietys with various nucleotide sequences and various lengths as the sense strands.

FIG. 5 shows the results in the use of siPolR2A-AS (SEQ ID NO: 2) as the antisense strand. DNA strands having one nucleotide mismatch and 5'-protruding moietys composed of T with various lengths were used as the DNA sense strands (Table 2-1, 7m and T3 to T15, SEQ ID NO: 19 to 24). The results demonstrated that sense strands having 5'-protruding moietys of various lengths all had high gene expression-suppressing activities compared to that not having any protruding moiety (FIG. 5). Furthermore, DNA sense strands 1 to 7 having random DNA sequences in their 5'-protruding moietys were used (Table 2-1, SEQ ID NOs: 25 to 31). As a result, a tendency of detecting higher activities in strands 6 and 7 having higher guanine (G) contents (G content: 47%) was observed (FIG. 5).

The results shown in FIG. 5 suggest that a sense strand having a 5'-protruding moiety, regardless of its length, has a higher gene expression-suppressing activity compared to that not having the 5'-protruding moiety and that a 5'-protruding moiety having a higher G content can be advantageous regardless of the sequence of the 5'-protruding moiety.

Figure 6:
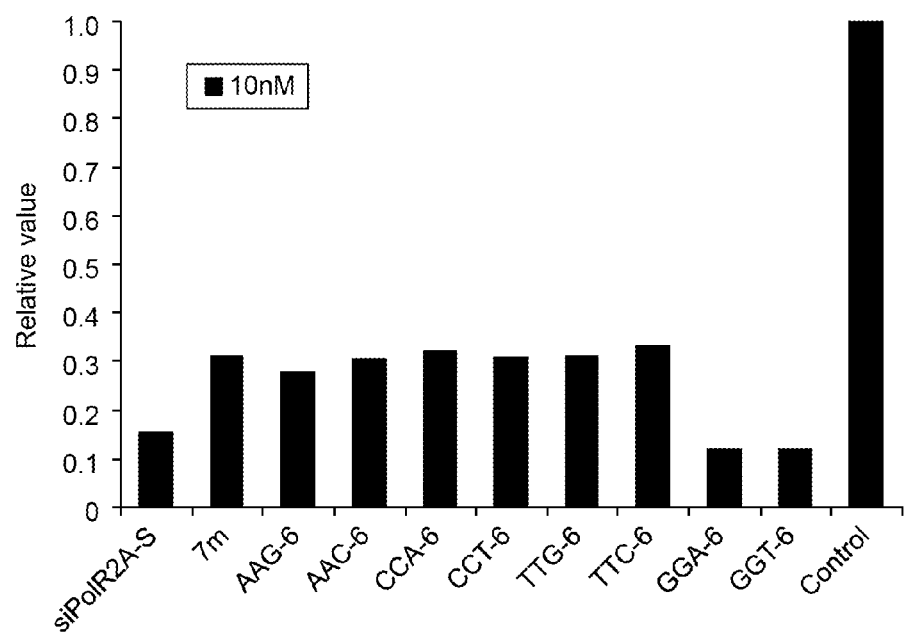
FIG. 6 shows the gene expression-suppressing activity of an RNA antisense strand (siPolR2A-AS) in cases of using DNA strands including 5'-protruding moietys having various G contents as the sense strands.

FIG. 6 shows gene expression-suppressing activities when the antisense strand was siPolR2A-AS as in above and the DNA sense strand was any of DNA strands having one nucleotide mismatch and 5'-protruding moietys having the same nucleotide lengths (6 nucleotides length) but various sequences of the nucleotides (Table 2-1, SEQ ID NOs: 32 to 39). The results demonstrated that GGA-6 and GGT-6 having higher G contents (G content: 67%) had higher activities (FIG. 6).

Figure 7:
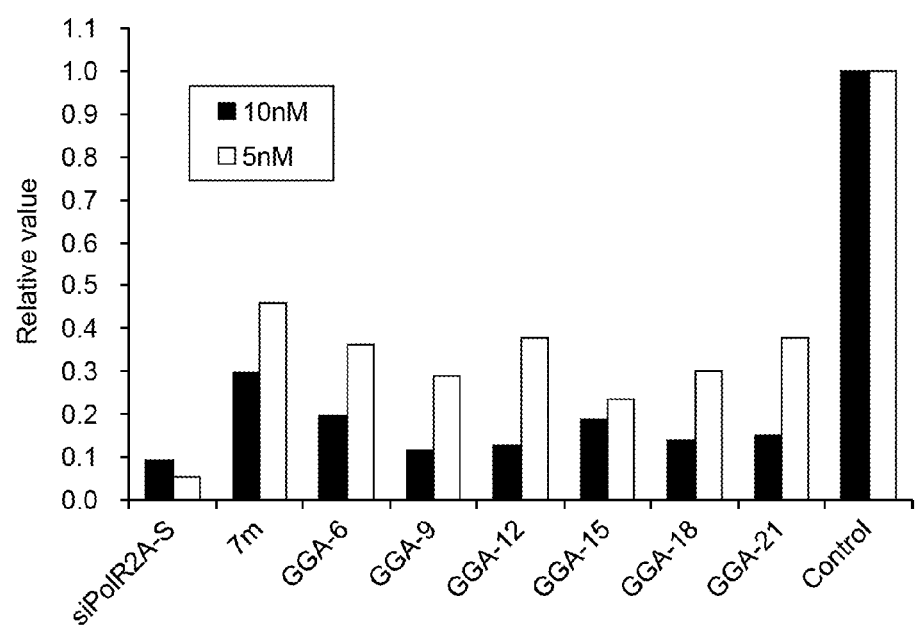
FIG. 7 shows the gene expression-suppressing activity of an RNA antisense strand (siPolR2A-AS) in cases of using DNA strands including St-protruding moietys of various nucleotide lengths as the sense strands.

FIG. 7 shows gene expression-suppressing activities when the antisense strand was siPolR2A-AS as in above and the sense strands was any of DNA strands having one nucleotide mismatch and 5'-protruding moietys with various nucleotide lengths composed of guanine (G) and adenine (A) containing the same G-contents (67%) (Table 2-1, GGA-6 to GGA-21, SEQ ID NOs: 38 and 40 to 44). The results demonstrated a tendency that a DNA sense strand having a 5'-protruding moiety, regardless of its length, has a higher activity compared to that not having the 5'-protruding moiety (FIG. 7).

The results above are summarized as follows: It was suggested that a double-stranded nucleic acid molecule composed of an RNA antisense strand and a DNA sense strand having a 5'-protruding moiety has a gene expression-suppressing activity substantially the same as that of a typical double-stranded RNA and that a higher G content of the 5'-protruding moiety gives a higher activity regardless of the length and the sequence of the nucleotides of the 5'-protruding moiety. Furthermore, it was suggested that the 5'-protrusion of a DNA sense strand and the mismatch between the antisense strand and the sense strand synergistically contribute to an increase in gene expression-suppressing activity.

(3) Further Investigation of Molecules Having Various Protruding Single-Stranded Moietys The gene expression-suppressing activity was investigated by further modifying the protrusion moiety. Herein, siPolR2A-AS was used as the antisense strand, and the protruding single-stranded moiety of the DNA sense strand was modified. The activity was measured as follows.

HEK293T cells were seeded in a 96-well plate at 120000 cells/well. On the following day, the cells were transfected with a double-stranded nucleic acid molecule (5 nM), the aforementioned plasmid pCAGGS-AFP (5 ng) expressing GFP, and the pDsRed2-siPolR2A target (5 ng), using MultiFectam (Promega Corporation). On the next day, the culture medium was replaced with a fresh one. After further one day, the cells were pulverized and extracted with an RIPA buffer, followed by centrifugation. The fluorescent intensity of the supernatant was measured as described above. The activity was evaluated with normalized DsRed2/GFP ratio (relative value).

Figure 9:
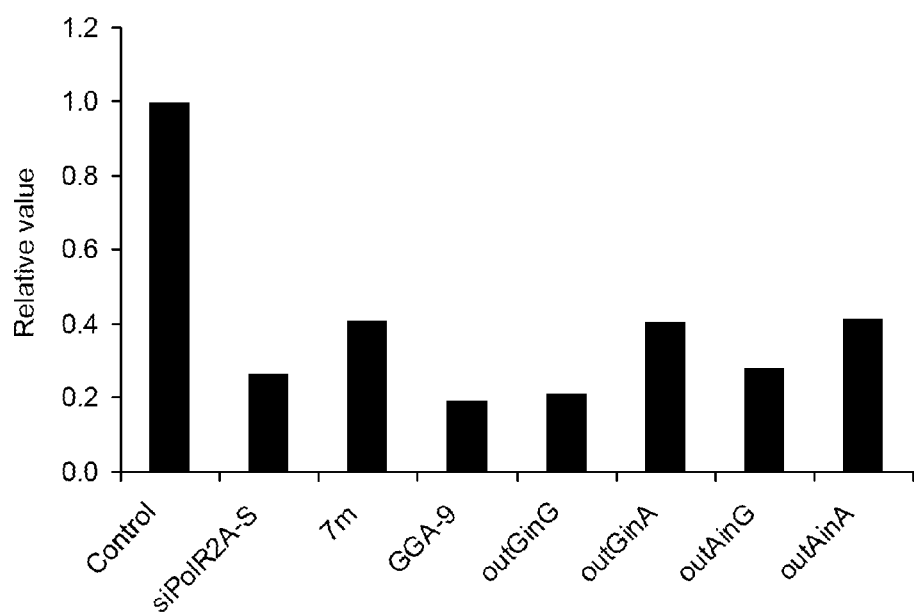
FIG. 9 shows the gene expression-suppressing activity of an RNA antisense strand (siPolR2A-AS) in cases of using DNA strands including various 5'-protruding moietys as the sense strands.

FIG. 9 shows the activities of molecules having G-rich regions at the 5'-end side and/or complementary moiety side of the protruding moiety. The structures of the molecules used are shown in FIG. 8. The activities were substantially the same regardless of the positions of the G-rich regions. It was also revealed that even if a protruding moiety has a conformation, the activity is maintained.

Figure 10:
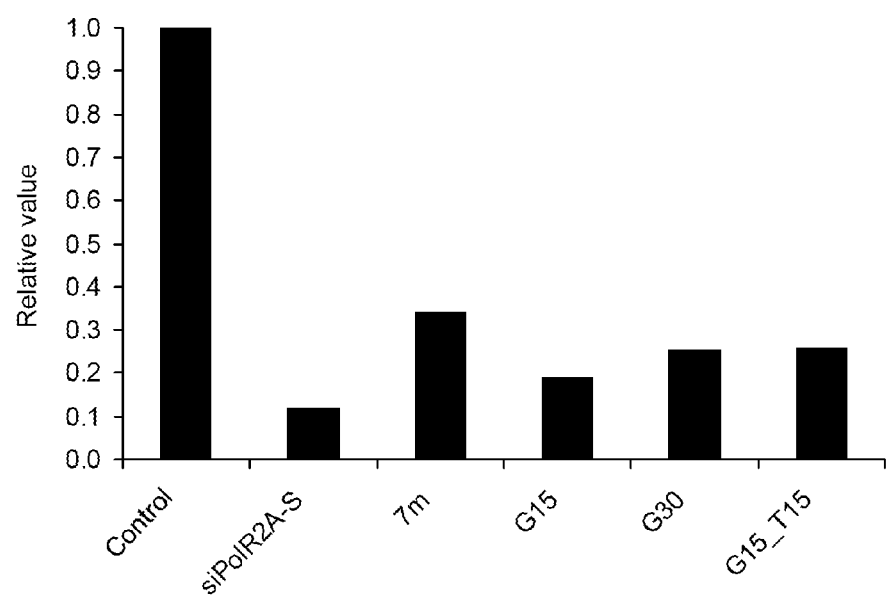
FIG. 10 shows the gene expression-suppressing activity of an RNA antisense strand (siPolR2A-AS) in cases of using DNA strands including various 5'-protruding moietys as the sense strands.

FIG. 10 shows the results in the cases of the whole protruding moiety consisting of G-rich regions and a protruding moiety having a G-rich region at the 5'-end (Table 2-2, G15, G30, and G15 J15. SEQ ID NOs: 66 to 68). A protruding moiety partially having a G-rich region also showed a high activity similar to that in the case of the whole protruding moiety consisting of G-rich regions.

Figure 12:
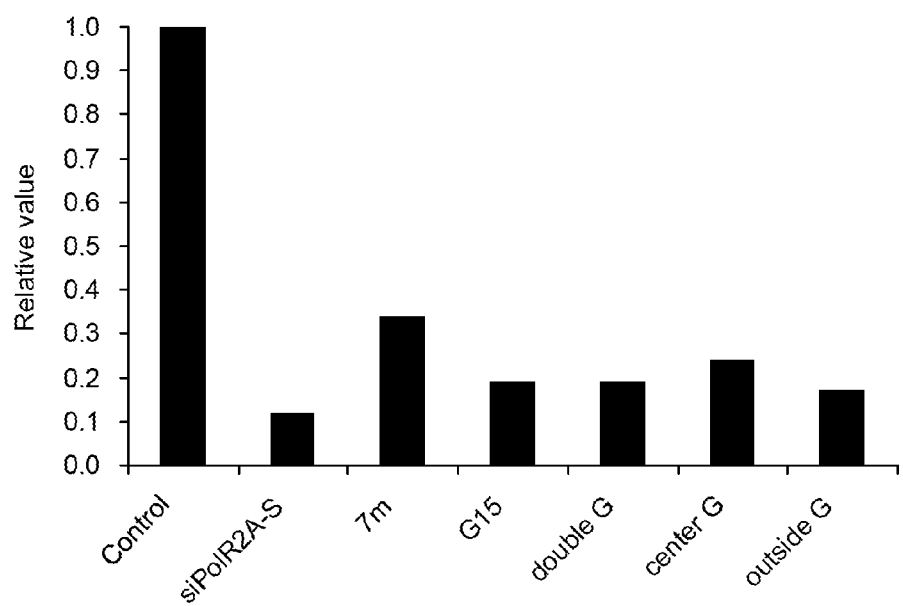
FIG. 12 shows the gene expression-suppressing activity of an RNA antisense strand (siPolR2A-AS) in cases of using DNA strands including various 5'-protruding moietys as the sense strands.

FIG. 12 shows the results in the cases of protruding moietys forming loop structures having one or more G-rich regions. The structures of the molecules used are shown in FIG. 11. High activities were observed in all of the molecules.

Figure 2:
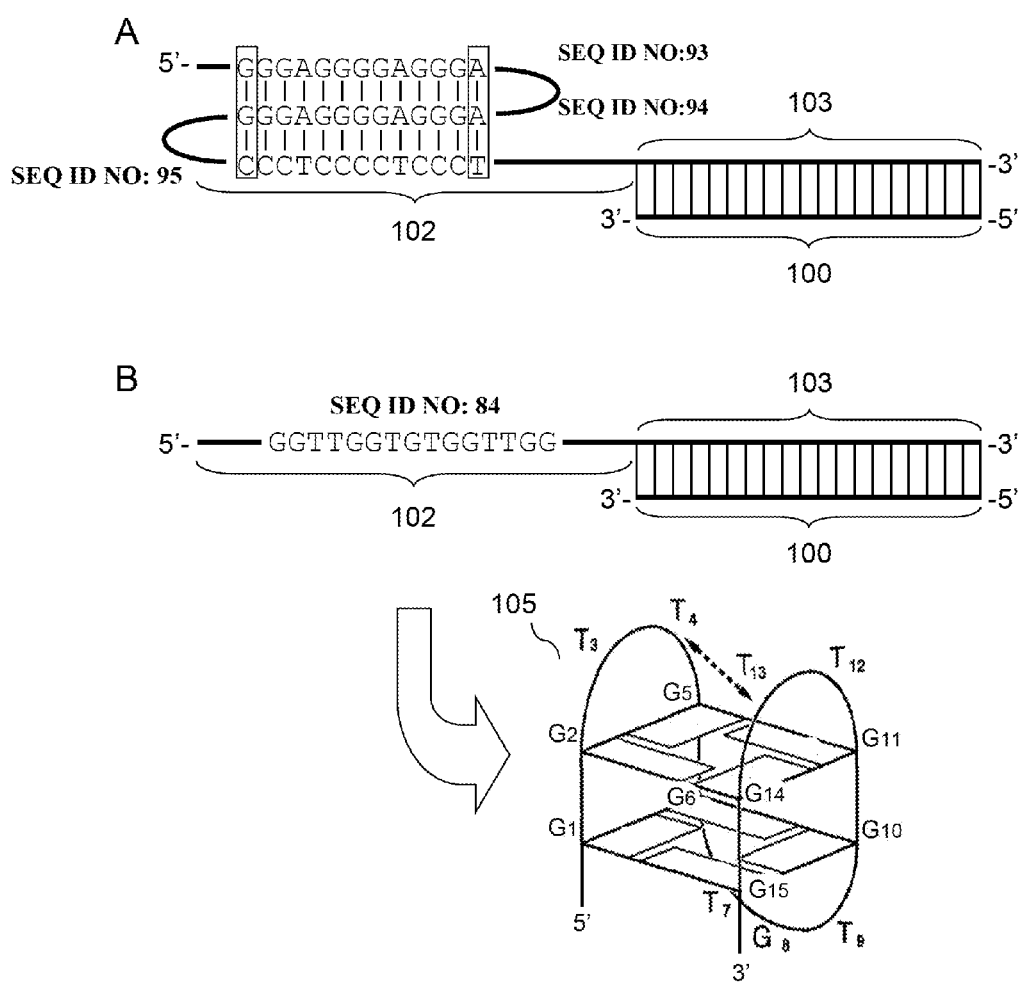
FIG. 2 shows conceptual diagrams illustrating the constitutions of double-stranded nucleic acid molecules according to the present invention. Diagram (A) shows an example of a triplex structure formed by a specific sequence in the protruding single-stranded moiety, wherein the triplex is formed of three nucleic acid strands by base pairing among three nucleotides (GGC or AAT) surrounded by frames among the nucleotide sequences of three rows of nucleic acid strands shown in the diagram; and diagram (B) shows an example of a quadruplex structure formed by a specific sequence in the protruding single-stranded moiety, wherein the G-quartet (105) is formed by the guanine-rich sequence.
Figure 13:
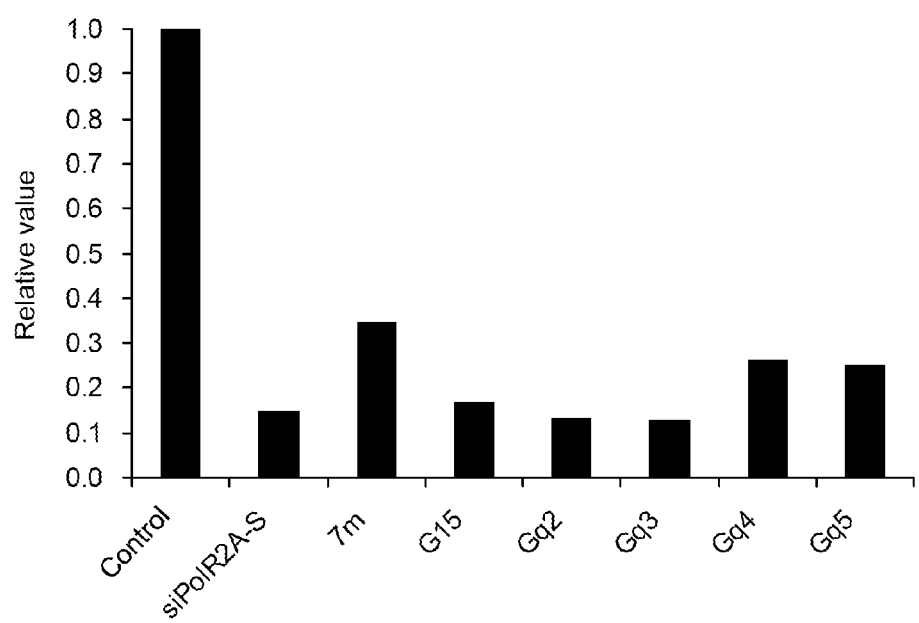
FIG. 13 shows the gene expression-suppressing activity of an RNA antisense strand (siPolR2A-AS) in cases of using DNA strands including various 5'-protruding moietys as the sense strands.

FIG. 13 shows the results in the cases of protruding moietys forming G-quartet structures (Table 2-2, Gq2 to Gq5, SEQ ID NOs: 72 to 75). Gq2 means that two plane structures of guanine are stacked on each other as shown in FIG. 2, and, similarly, Gq3 means three plane structures are stacked on each other. Each case showed a high activity.

Figure 14:
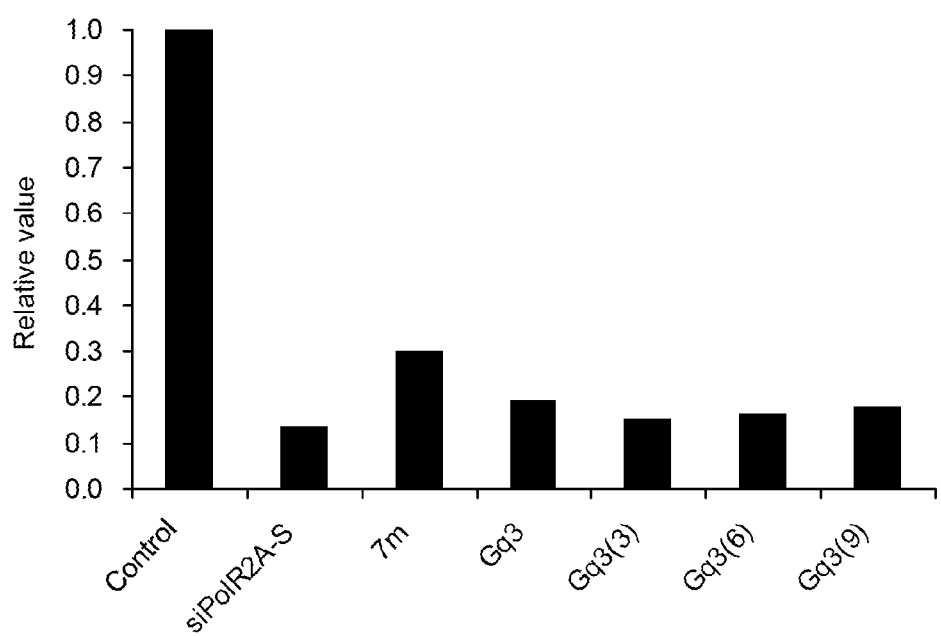
FIG. 14 shows the gene expression-suppressing activity of an RNA antisense strand (siPolR2A-AS) in cases of using DNA strands including various 5'-protruding moietys as the sense strands.

FIG. 14 shows the results in the cases of having spacers of thymine (T) between the G-quartet structures and the complementary moietys of protruding moietys (Table 2-2, Gq3(3) to Gq3(9). SEQ ID NOs: 76 to 78). Each case showed a high activity.

The results described above revealed that the 5'-protruding moiety of the sense strand having one or more G-rich regions provides a high activity and that the activity is not affected by the position of the region in the protruding moiety. In addition, it was revealed that a protruding moiety having a conformation such as a G-quartet is also preferred.

Example 2

RNA Sense Strand Having 5'-Protruding Moiety (1) High Gene Expression-Suppressing Activity in Use of RNA Sense Strand Having 5'-Protruding Moiety Example 1 revealed that the gene expression-suppressing activity by an RNA antisense strand can be obtained by using a DNA sense strand having a 5'-protruding moiety. In Example 2, the activities of RNA sense strands having 5'-protruding moietys would be evaluated.

FIG. 15 shows the results in the use of miR-143 as the antisense strand. As the RNA sense strand, natural miR-143*, a complementary strand to miR-143 (Table 1-1, R143(comp), SEQ ID NO: 45), an RNA strand having one nucleotide mismatch (Table 1-1, R143(4m), SEQ ID NO: 46), or an RNA strand having one nucleotide mismatch and a 5'-protruding moiety with a length of 16 nucleotides (Table 1-1, R143(4m)16L, SEQ ID NO: 47) was used. As a result, unexpectedly, the use of an RNA sense strand having a 5'-protruding moiety (R143(4m)16L) provides a significantly high gene expression-suppressing activity compared to natural miRNA* (FIG. 15A). Surprisingly, an amount of 100 µM showed about 7 times high gene expression-suppressing activity (FIG. 15A., comparison between miR-143* and R143 (4m)16L).

Measurement of gene expression-suppressing activities at further low concentrations demonstrated that an RNA sense strand having a 5'-protruding moiety has a suppressing activity of about 0.2 even at a concentration of 50 µM and that a sufficient effect can be obtained even at such a low concentration (FIG. 15B). The comparison of IC50 demonstrated that although the IC50 was 53.9 µM in the natural type (miR143*), the IC50 in the protrusion type (R143(4m) 16L) was 24.4 µM, and showed more than twice as high activity (FIG. 15B).

(2) Investigation of length of protruding single-stranded moiety

Various RNA sense strands were produced and were further evaluated for activities.

Figure 16:
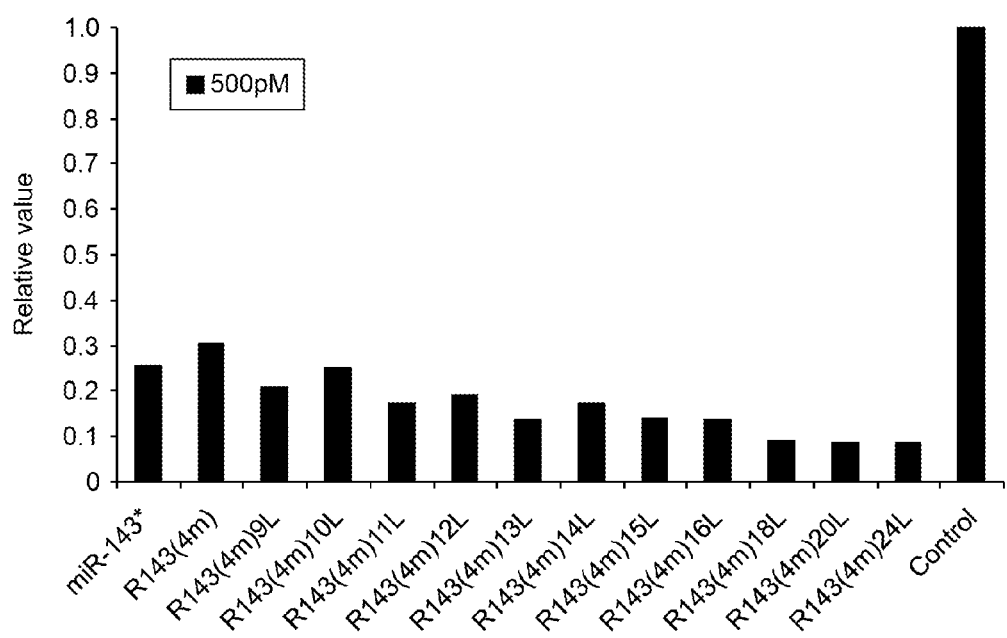
FIG. 16 shows the gene expression-suppressing activity of an RNA antisense strand (miR-143) in cases of using RNA strands including 5'-protruding moietys of various nucleotide lengths as the sense strands.
Figure 17:
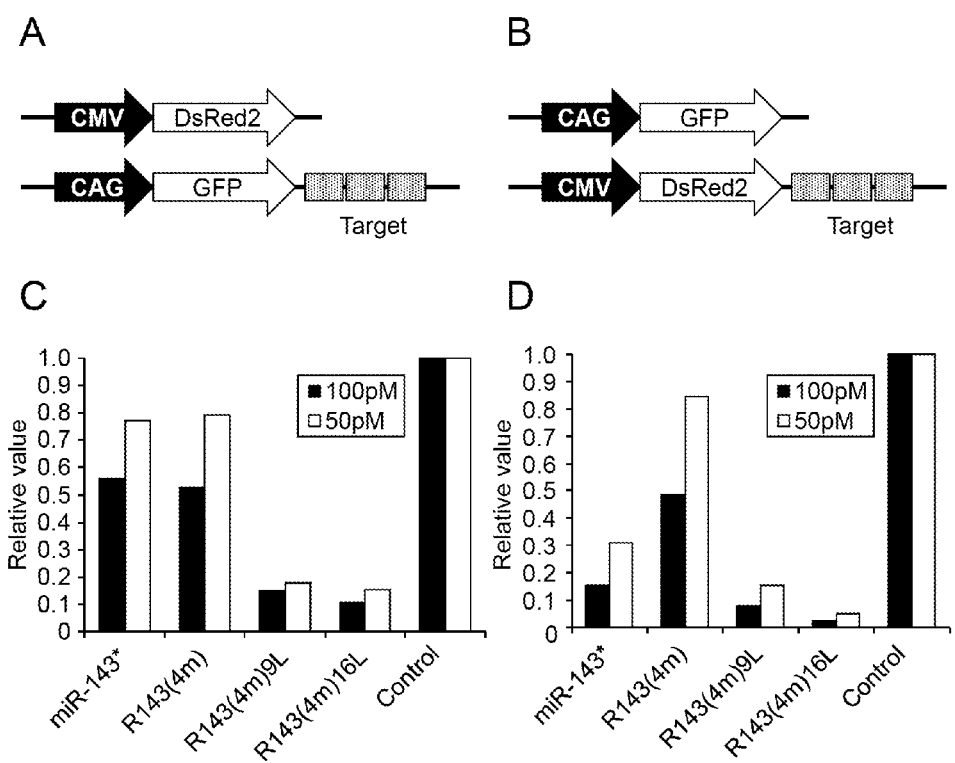
FIG. 17 shows the comparative results in two assay systems. Diagrams (A) and (B) schematically show the plasmids used in the assay systems, and graphs (C) and (D) show the results in the assay systems, respectively.

FIG. 16 shows the results in the use of miR-143 as the antisense strand. RNA strands having one nucleotide mismatch and 5'-protruding moietys with various lengths were used as the RNA sense strands (Table 1-1, R143(4m), R143(4m)9L to 24L, SEQ ID NOs: 46 to 57). The results demonstrated that RNA sense strands having 5'-protruding moietys of various lengths all had high gene expression-suppressing activities compared to that not having any protruding moiety (FIG. 16).

(3) Investigation of Change in Gene Expression-Suppressing Activity Depending on Assay System In the above-described examples, unless otherwise specified, the activities were evaluated in accordance with the above-described "Method of measuring gene expression-suppressing activity". In order to confirm that the same results are obtained by other assay systems, DsRed2, which was used for evaluating the gene expression-suppressing activity, was replaced with the GFP that was used for normalization. That is, pDsRed2-C1 (Clontech Laboratories, Inc.) was used as the plasmid for normalization, and pCA-GGS-AFP-miR143 target was used as the plasmid for activity evaluation (FIG. 17A). The pCAGGS-AFP-miR143 target was produced by linking a molecule prepared by annealing the DNA strands of above-mentioned SEQ ID NOs: 4 and 5 to the blunt end on the 3'-side of the GFP gene of pCAGGS-AFP cleaved with EcoRV. miR-143 was used as the antisense strand, and as the sense strand, an RNA strand not having any 5'-protruding moiety (Table 1-1, R143(4m), SEQ ID NO: 46) or an RNA strand having a 5'-protruding moiety with a length of 9 or 16 nucleotides (Table 1-1, R143(4m)9L, SEQ ID NO: 48; R143(4m)16L, SEQ ID NO: 47) was used. The results demonstrated a tendency that the same activities as those in the above-described assay system (FIG. 17D) are obtained also in another assay system (FIG. 17C) and demonstrated that the use of an RNA sense strand having a 5'-protruding moiety provides a significantly high activity. This supports the validity of the results in the above-described activity evaluation.

Example 3

DNA/RNA Chimera Sense Strand Having 5'-Protruding Moiety

Gene expression-suppressing activities would be investigated for the cases that sense strands were DNA/RNA chimeras, that is, various combinations of deoxyribonucleotides and ribonucleotides were used as the complementary moiety to the antisense strand and the 5'-protruding moiety of the sense strand.

Figure 18:
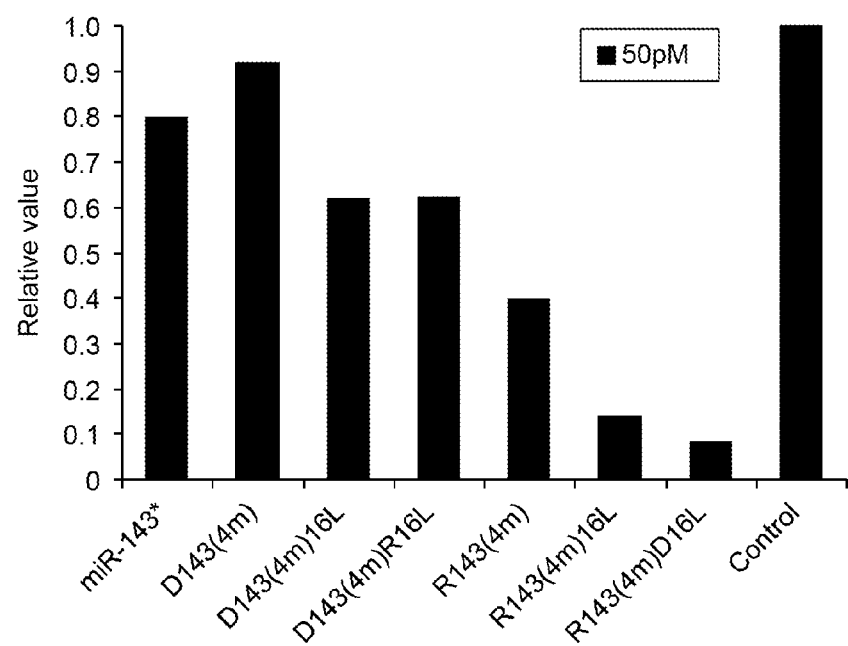
FIG. 18 shows the gene expression-suppressing activity of an RNA antisense strand (miR-143) in cases of using chimeric RNA-DNA strands as the sense strands.

The results are shown in FIG. 18. miR-143 was used as the antisense strand. As the sense strand, a sense strand having a DNA as the complementary moiety to the antisense strand and not having any 5'-protruding moiety (Table 1-2, D143(4m), SEQ ID NO: 11) or having a DNA or RNA as the 5'-protruding moiety (Table 1-2, D143(4m)16L, SEQ ID NO: 12; D143(4m)R16L, SEQ ID NO: 58) was used. Reversely, a sense strand having an RNA as the complementary moiety to the antisense strand and not having any 5'-protruding moiety (Table 1-2, R143(4m), SEQ ID NO: 46) or having an RNA or DNA as the 5'-protruding moiety (Table 1-2, R143(4m)16L, SEQ ID NO: 47; R143(4m) D16L, SEQ ID NO: 59) was used.

When the complementary moiety was a DNA, in both D143(4m)16L (5'-protrusion of a DNA) and D143(4m) R16L (5'-protrusion of an RNA), the activities were higher than that of D143(4m). Similarly, when the complementary moiety was an RNA, in both R143(4m)16L (5'-protrusion of an RNA) and R143(4m)D16L (5'-protrusion of a DNA), the activities were higher than that of R143(4m). These results suggest that whether the 5'-protruding moiety is a DNA or RNA is not important for the activity. Furthermore, in R143(4m)16L and R143(4m)D16L having complementary moietys of RNAs, the activities were high. This suggests that it is important for activity that the complementary moiety to the antisense strand be an RNA.

Comparative Example

Figure 19:
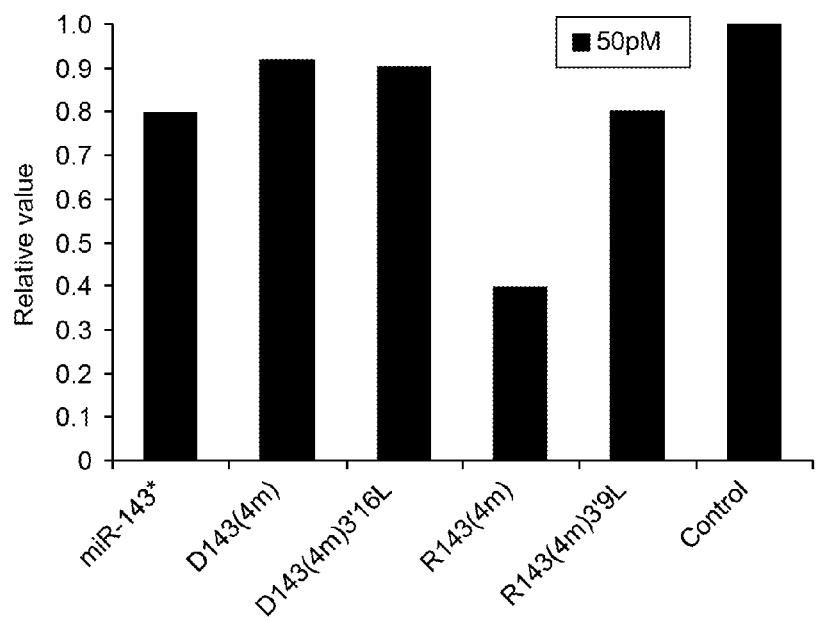
FIG. 19 shows the gene expression-suppressing activity of an RNA antisense strand (miR-143) in cases of using RNA or DNA strands including 3'-protruding moietys as the sense strands.

FIG. 19 shows the results of investigation of activities with sense strands having 3'-protruding moietys. The oligonucleotides used are shown in Table 1-2. The results demonstrate that in both RNA and DNA strands, effective gene expression-suppressing activities were not observed even if the sense strands had protrusion moietys when the protrusion moietys were at the 3'-ends of the sense strands.

Example 4

Effect on Endogenous Gene in Human HeLa-S3 Cells

In order to investigate the effect of suppressing endogenous gene expression, an experiment of gene suppression was performed using a DNA-dependent RNA polymerase PolR2A gene of human HeLa-S3 cells as a target. RNA polymerase PolR2 is an enzyme bearing transcription of mRNA. It is supposed that the proliferation of cells is decreased or cells become lethal by highly suppressing the expression of the PolR2A gene, which encodes the subunit, with a high concentration of a double-stranded nucleic acid molecule in the absence of foreign targets such as a reporter gene.

The effect of controlling gene expression was investigated by the following method. HeLa-S3 cells (8000 cells) were seeded in a 96-well plate. On the next day, the cells were transfected with 50 nM of antisense strand siPolR2A-AS (SEQ ID NO: 2, Table 2-1) and 50 nM of a double-stranded nucleic acid molecule composed of sense strand siPolR2A-S (SEQ ID NO: 18, Table 2-1) or gga-5 (SEQ ID NO: 79, Table 2-2) or the above-described control siRNA double-stranded nucleic acid molecule (SEQ ID NOs: 8 and 9) using X-treme GENE siRNA Transfection Reagent (Roche Applied Science). Further two days after, the survival rate of the cells was measured with Cell Counting Kit-8 (Dojindo Laboratories).

Figure 20:
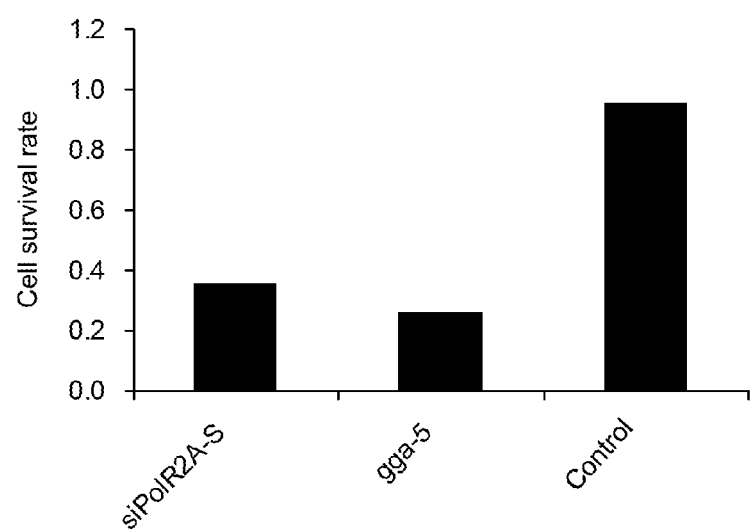
FIG. 20 shows the effect of suppressing the gene expression of an endogenous RNA polymerase PolR2A gene in human HeLa-S3 cells.

As shown in FIG. 20, the use of the double-stranded nucleic acid molecule (including sense strand gga-5) of the present invention decreased the survival rate of cells as in usual siRNA (including sense strand siPolR2A-S). Accordingly, it has been revealed that the double-stranded nucleic acid molecule of the present invention also has an effect of suppressing an endogenous gene expression. This suggests that the double-stranded nucleic acid molecule of the present invention is a versatile tool that can be applied to an endogenous gene target.

Example 5

Tumor-Suppressing Effect in Human Cancer Cell

It has been reported that miR-143 introduced into cancer cells inhibits cell proliferation to show a tumor-suppressing effect (Akao Y, et al., 2010, Cancer Gene Ther., 17, 398-408). Whether the double-stranded nucleic acid molecule of the present invention functions in cancer cells to show a tumor-suppressing effect, as in natural miRNA, was investigated by the following method. Human colorectal cancer DLD-1 cells (8000 cells) were seeded in a 96-well plate. On the next day, the cells were transfected with 50 nM of antisense strand miR-143 (SEQ ID NO: 1, Table 1-1) and 50 nM of a double-stranded nucleic acid molecule composed of sense strand miR-143* (SEQ ID NO: 10, Table 1-1) or R143(4m)D16L (SEQ ID NO: 59, Table 1-2) or the above-described control siRNA double-stranded nucleic acid molecule (SEQ ID NOs: 8 and 9) using Lipofectamine™ RNAiMAX (Invitrogen). Further three days after, the number of cells in each well was counted to determine the number of cells per unit area (cells/mm$^2$).

Figure 21:
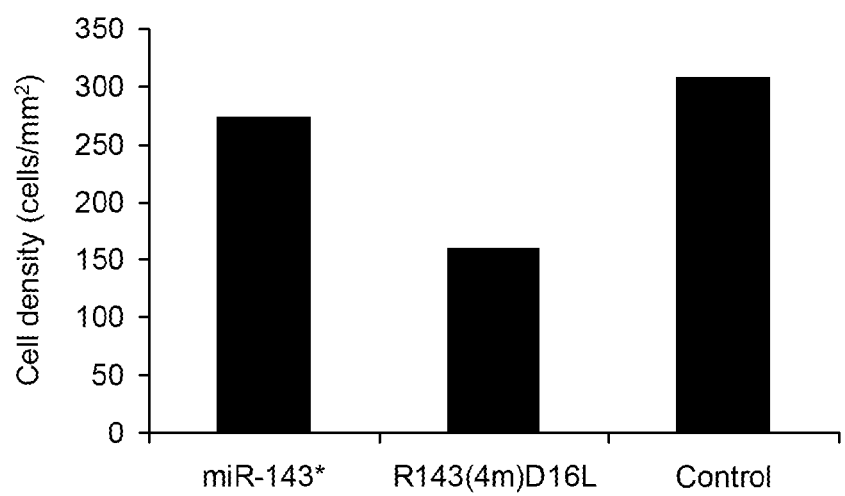
FIG. 21 shows the cytostatic effects in human colon cancer DLD-1 cells.

The results shown in FIG. 21 demonstrate that the double-stranded nucleic acid molecule of the present invention containing sense strand R143(4m)D16L has a cancer cell proliferation-suppressing effect higher than that of natural miRNA containing sense strand miR-143*. This means that a cancer therapeutic agent containing the double-stranded nucleic acid molecule of the present invention as an active ingredient is more effective than that of natural miRNA.

Example 6

Influence on Innate Immune Response

It is generally known that usual siRNA causes innate immune response by recognition of double-stranded RNA. Excess response of an innate immune system is an obstacle in drug development. Whether the double-stranded nucleic acid molecule of the present invention causes an innate immune response was investigated by the following method. HeLa-S3 cells (8000 cells) were seeded in a 96-well plate. On the next day, the cells were transfected with three types of 40 nM of double-stranded nucleic acid molecule composed of an antisense strand (siGFP-AS, SEQ ID NO: 80) and a sense strand (siGFP-S, SEQ ID NO: 81; siGFP(7m), SEQ ID NO: 82; or siGFP(7m)12L, SEQ ID NO: 83) shown in Table 3 or 50 ng of poly I:C, using X-treme GENE siRNA Transfection Reagent (Roche Applied Science). After 9 hours, the total RNA was collected and was subjected to quantitative RT-PCR (qRT-PCR) to investigate the expression levels of IFNβ, IP10, and OAS1 mRNA, which are induced in innate immunity. Combinations of primers below on this occasion were IFNβ forward (5'-TCACTGTGC-CTGGACCATAG-3', SEQ ID NO: 85) and IFNβ reverse (5'-CAGCATCTGCTGGTTGAAGA-3', SEQ ID NO: 86); OAS1 forward (5"-GCAGAAGAGGACTGGACCTG-3', SEQ ID NO: 87) and OAS1 reverse (5'-TAGAAGGCCA-GGAGTCAGGA-3', SEQ ID NO: 88); and IP10 forward (5'-GCTCTACTGAGGTGCTATGTTC-3', SEQ ID NO: 89) and IP10 reverse (5'-CCCTTGGAAGATGGGAAAGGT-3', SEQ ID NO: 90). The results were corrected with respect to endogenous control GAPDH by using primers: GAPDH forward (5'-TCCCATCACCATCTTCCA-3', SEQ ID NO: 91) and GAPDH reverse (5'-CATCACGCCACAGTTTCC-3', SEQ ID NO: 92).

The results shown in FIG. 22 demonstrate that the double-stranded nucleic acid molecule (including sense strand siGFP(7m)12L) of the present invention of which the sense strand is a DNA, does not cause an innate immune response or causes at low level compared to usual siRNA (including sense strand siGFP-S). This suggests that the double-stranded nucleic acid molecule of the present invention causes fewer side effects such as an innate immune response and can therefore be a highly safe active ingredient of a pharmaceutical composition.

All publications, patents, and patent applications cited in the present specification are hereby incorporated by reference in their entirety.

INDUSTRIAL APPLICABILITY

Gene expression control can be highly efficiently achieved by using the double-stranded nucleic acid molecule of the present invention. In particular, a DNA strand can be used as a sense strand. In such a case, a decrease in cost can be expected compared to the use of an RNA strand. A pharmaceutical composition using the double-stranded nucleic acid molecule can be expected to have an effect in prophylaxis and/or therapy of a variety of diseases.

SEQUENCE LISTING FREE TEXT

SEQ ID NOs: 8, 9, 58, AND 59: synthetic DNA/RNA chimeras

SEQ ID NOs: 1, 2, 10, 18, 45 to 57, 61, and 79 to 81: synthetic RNAs

SEQ ID NOs: 3 to 7, 11 to 17, 19 to 44, 60, 62 to 78, and 82 to 84: synthetic DNAs SEQ ID NOs: 85 to 92: primers

---

The invention claimed is:

1. A double-stranded nucleic acid molecule for gene expression control, comprising:

an antisense strand of 18 to 28 nucleotides; and a sense strand including a complementary moiety composed of a sequence sufficiently complementary to the antisense strand and a protruding single-stranded 5'-end moiety, wherein the sense strand and the antisense strand form base pairs via the complementary moiety, the protruding single-stranded moiety comprises one or more G-rich regions, and wherein the protruding single-stranded moiety forms a triplex or a quadruplex within the protruding single-stranded moiety.

2. The double-stranded nucleic acid molecule according to claim 1, wherein the antisense strand is composed of ribonucleotides.

3. The double-stranded nucleic acid molecule according to claim 1, wherein the antisense strand is a miRNA.

4. The double-stranded nucleic acid molecule according to claim 1, wherein the antisense strand is composed of a sequence sufficiently complementary to a target sequence of a target gene.

5. The double-stranded nucleic acid molecule according to claim 1, wherein the complementary moiety included in the sense strand is composed of ribonucleotides.

6. The double-stranded nucleic acid molecule according to claim 1, wherein the sense strand is composed of ribonucleotides.

7. The double-stranded nucleic acid molecule according to claim 1, wherein the sense strand is composed of deoxyribonucleotides.

8. The double-stranded nucleic acid molecule according to claim 1, wherein the protruding single-stranded moiety has a G content of 30% to 80% based on the length of the protruding single-stranded moiety.

9. The double-stranded nucleic acid molecule according to claim 1, wherein the complementary moiety included in the sense strand has 0 to 30% of nucleotide mismatches with the antisense strand.

10. The double-stranded nucleic acid molecule according to claim 1, wherein the antisense strand comprises the nucleotide sequence set forth in SEQ ID NO: 1.

11. The double-stranded nucleic acid molecule according to claim 1, wherein the antisense strand comprises the nucleotide sequence set forth in SEQ ID NO: 2.

12. A double-stranded nucleic acid molecule for gene expression control, comprising:
   an antisense strand of 18 to 28 nucleotides; and
   a sense strand including a complementary moiety composed of a sequence sufficiently complementary to the antisense strand a protruding single-stranded 5'-end moiety composed of 2 to 100 nucleotides,
   wherein the sense strand and the antisense strand form base pairs via the complementary moiety,
   the protruding single-stranded moiety comprises one or more G-rich regions,
   the antisense strand comprises the nucleotide sequence set forth in SEQ ID NO: 1, and
   the sense strand comprises the nucleotide sequence set forth in any of SEQ ID NOs: 12, 14, 15, 17, and 47 to 59.

13. The double-stranded nucleic acid molecule according to claim 12, wherein the sense strand comprises the nucleotide sequence set forth in SEQ ID NO: 57.

14. A double-stranded nucleic acid molecule for gene expression control, comprising:
   an antisense strand of 18 to 28 nucleotides; and
   a sense strand including a complementary moiety composed of a sequence sufficiently complementary to the antisense strand and a protruding single-stranded 5'-end moiety composed of 2 to 100 nucleotides, wherein
   the sense strand and the antisense strand form base pairs via the complementary moiety, the protruding single-stranded moiety comprises one or more G-rich regions,
   the antisense strand comprises the nucleotide sequence set forth in SEQ ID NO: 2, and
   the sense strand comprises the nucleotide sequence set forth in any of SEQ ID NOs: 21 to 44, 66, 72 to 74, and 76.

15. The double-stranded nucleic acid molecule according to claim 14, wherein the sense strand comprises the nucleotide sequence set forth in SEQ ID NO: 40.

16. A pharmaceutical composition comprising a double-stranded nucleic acid molecule according to claim 1 as an active ingredient.

17. The pharmaceutical composition according to claim 16, comprising a pharmaceutically acceptable carrier.

18. A method of producing a double-stranded nucleic acid molecule according to claim 1, the method comprising the steps of:
   (a) designing an antisense strand comprising a sequence sufficiently complementary to a target sequence of a target gene or selecting a miRNA as an antisense strand;
   (b) designing a sense strand comprising a complementary moiety composed of a sequence sufficiently complementary to the antisense strand and a protruding single-stranded 5'-end moiety;
   (c) synthesizing the antisense strand and the sense strand; and
   (d) forming base pairs between the synthesized antisense strand and the sense strand.

19. A method of controlling gene expression in a cell, tissue, or individual, the method comprising the step of:
   introducing a double-stranded nucleic acid molecule according to claim 1 into the cell, tissue, or individual.

* * * * *

UNITED STATES PATENT AND TRADEMARK OFFICE
CERTIFICATE OF CORRECTION

PATENT NO. : 9,593,331 B2
APPLICATION NO. : 14/355711
DATED : March 14, 2017
INVENTOR(S) : Akira Tachibana and Toshizumi Tanabe Page 1 of 1

It is certified that error appears in the above-identified patent and that said Letters Patent is hereby corrected as shown below:

Column 63, Line 12, in Claim 12, "antisense strand a protruding" should be --antisense strand and a protruding--.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 95

<210> SEQ ID NO 1
<211> LENGTH: 21
<212> TYPE: RNA
<213> ORGANISM: Artificial sequence
<220> FEATURE:
<223> OTHER INFORMATION: Synthetic RNA

<400> SEQUENCE: 1
cucgauguca cgaaguagag u                                            21
```

<210> SEQ ID NO 2
<211> LENGTH: 25
<212> TYPE: RNA
<213> ORGANISM: Artificial sequence
<220> FEATURE:
<223> OTHER INFORMATION: Synthetic RNA

<400> SEQUENCE: 2
guugcaacuc cuuccacuga cgguu                                         25

<210> SEQ ID NO 3
<211> LENGTH: 57
<212> TYPE: DNA
<213> ORGANISM: Artificial sequence
<220> FEATURE:
<223> OTHER INFORMATION: Synthetic DNA

<400> SEQUENCE: 3
agatctcgag aagcttagat atcgtcgacc cgggatccac cggatctaga taactga      57

<210> SEQ ID NO 4
<211> LENGTH: 67
<212> TYPE: DNA
<213> ORGANISM: Artificial sequence
<220> FEATURE:
<223> OTHER INFORMATION: Synthetic DNA

<400> SEQUENCE: 4
gtaggagcta cagtgcttca tctcagagct acagtgcttc atctcagagc tacagtgctt   60
catctca                                                             67

<210> SEQ ID NO 5
<211> LENGTH: 67
<212> TYPE: DNA
<213> ORGANISM: Artificial sequence
<220> FEATURE:
<223> OTHER INFORMATION: Synthetic DNA

<400> SEQUENCE: 5
tgagatgaag cactgtagct ctgagatgaa gcactgtagc tctgagatga agcactgtag   60
ctcctac                                                             67

<210> SEQ ID NO 6
<211> LENGTH: 79
<212> TYPE: DNA
<213> ORGANISM: Artificial sequence
<220> FEATURE:
<223> OTHER INFORMATION: Synthetic DNA

<400> SEQUENCE: 6
gtagcaacgt tgaggaaggt gactgccaac aacgttgagg aaggtgactg ccaacaacgt   60
tgaggaaggt gactgccaa                                                79

<210> SEQ ID NO 7
<211> LENGTH: 79
<212> TYPE: DNA
<213> ORGANISM: Artificial sequence
<220> FEATURE:
<223> OTHER INFORMATION: Synthetic DNA

<400> SEQUENCE: 7
ttggcagtca ccttcctcaa cgttgttggc agtcaccttc ctcaacgttg ttggcagtca   60
ccttcctcaa cgttgctac                                              79

<210> SEQ ID NO 8
<211> LENGTH: 21
<212> TYPE: DNA
<213> ORGANISM: Artificial sequence
<220> FEATURE:
<221> NAME/KEY: RNA
<222> LOCATION: (1)..(19)
<223> OTHER INFORMATION: Synthetic DNA RNA chimera

<400> SEQUENCE: 8
gcgcgcuuug uaggauucgt t                                           21

<210> SEQ ID NO 9
<211> LENGTH: 21
<212> TYPE: DNA
<213> ORGANISM: Artificial sequence
<220> FEATURE:
<221> NAME/KEY: RNA
<222> LOCATION: (1)..(19)
<223> OTHER INFORMATION: Synthetic DNA RNA chimera

<400> SEQUENCE: 9
cgaauccuac aaagcgcgct t                                           21

<210> SEQ ID NO 10
<211> LENGTH: 22
<212> TYPE: RNA
<213> ORGANISM: Artificial sequence
<220> FEATURE:
<223> OTHER INFORMATION: Synthetic RNA

<400> SEQUENCE: 10
ggugcagugc ugcaucucug gu                                          22

<210> SEQ ID NO 11
<211> LENGTH: 21
<212> TYPE: DNA
<213> ORGANISM: Artificial sequence
<220> FEATURE:
<223> OTHER INFORMATION: Synthetic DNA

<400> SEQUENCE: 11
gaggtacagt gcttcatctc a                                           21

<210> SEQ ID NO 12
<211> LENGTH: 37
<212> TYPE: DNA
<213> ORGANISM: Artificial sequence
<220> FEATURE:
<223> OTHER INFORMATION: Synthetic DNA

<400> SEQUENCE: 12
gcgtaggcgt tggagcgagg tacagtgctt catctca                          37

<210> SEQ ID NO 13
<211> LENGTH: 25
<212> TYPE: DNA
<213> ORGANISM: Artificial sequence
<220> FEATURE:
<223> OTHER INFORMATION: Synthetic DNA

<400> SEQUENCE: 13
gagcgaggta cagtgcttca tctca                                       25

<210> SEQ ID NO 14
<211> LENGTH: 29
<212> TYPE: DNA
<213> ORGANISM: Artificial sequence
<220> FEATURE:
<223> OTHER INFORMATION: Synthetic DNA

<400> SEQUENCE: 14
gttggagcga ggtacagtgc ttcatctca                                      29

<210> SEQ ID NO 15
<211> LENGTH: 33
<212> TYPE: DNA
<213> ORGANISM: Artificial sequence
<220> FEATURE:
<223> OTHER INFORMATION: Synthetic DNA

<400> SEQUENCE: 15
aggcgttgga gcgaggtaca gtgcttcatc tca                                 33

<210> SEQ ID NO 16
<211> LENGTH: 21
<212> TYPE: DNA
<213> ORGANISM: Artificial sequence
<220> FEATURE:
<223> OTHER INFORMATION: Synthetic DNA

<400> SEQUENCE: 16
gagctacagt gcttcatctc a                                              21

<210> SEQ ID NO 17
<211> LENGTH: 37
<212> TYPE: DNA
<213> ORGANISM: Artificial sequence
<220> FEATURE:
<223> OTHER INFORMATION: Synthetic DNA

<400> SEQUENCE: 17
gcgtaggcgt tggagcgagc tacagtgctt catctca                             37

<210> SEQ ID NO 18
<211> LENGTH: 25
<212> TYPE: RNA
<213> ORGANISM: Artificial sequence
<220> FEATURE:
<223> OTHER INFORMATION: Synthetic RNA

<400> SEQUENCE: 18
caacguugag gaaggugacu gccaa                                          25

<210> SEQ ID NO 19
<211> LENGTH: 25
<212> TYPE: DNA
<213> ORGANISM: Artificial sequence
<220> FEATURE:
<223> OTHER INFORMATION: Synthetic DNA

<400> SEQUENCE: 19
caacgtcgag gaaggtgact gccaa                                          25

<210> SEQ ID NO 20
<211> LENGTH: 28
<212> TYPE: DNA
<213> ORGANISM: Artificial sequence
<220> FEATURE:
<223> OTHER INFORMATION: Synthetic DNA

<400> SEQUENCE: 20
tttcaacgtc gaggaaggtg actgccaa                                          28

<210> SEQ ID NO 21
<211> LENGTH: 31
<212> TYPE: DNA
<213> ORGANISM: Artificial sequence
<220> FEATURE:
<223> OTHER INFORMATION: Synthetic DNA

<400> SEQUENCE: 21 tttttcaac gtcgaggaag gtgactgcca a                                       31

<210> SEQ ID NO 22
<211> LENGTH: 34
<212> TYPE: DNA
<213> ORGANISM: Artificial sequence
<220> FEATURE:
<223> OTHER INFORMATION: Synthetic DNA

<400> SEQUENCE: 22 ttttttttc aacgtcgagg aaggtgactg ccaa                                    34

<210> SEQ ID NO 23
<211> LENGTH: 37
<212> TYPE: DNA
<213> ORGANISM: Artificial sequence
<220> FEATURE:
<223> OTHER INFORMATION: Synthetic DNA

<400> SEQUENCE: 23
tttttttttt ttcaacgtcg aggaaggtga ctgccaa                                37

<210> SEQ ID NO 24
<211> LENGTH: 40
<212> TYPE: DNA
<213> ORGANISM: Artificial sequence
<220> FEATURE:
<223> OTHER INFORMATION: Synthetic DNA

<400> SEQUENCE: 24
tttttttttt tttttcaacg tcgaggaagg tgactgccaa                             40

<210> SEQ ID NO 25
<211> LENGTH: 42
<212> TYPE: DNA
<213> ORGANISM: Artificial sequence
<220> FEATURE:
<223> OTHER INFORMATION: Synthetic DNA

<400> SEQUENCE: 25
cctgaagttc atctgcacaa cgtcgaggaa ggtgactgcc aa                          42

<210> SEQ ID NO 26
<211> LENGTH: 42
<212> TYPE: DNA
<213> ORGANISM: Artificial sequence
<220> FEATURE:
<223> OTHER INFORMATION: Synthetic DNA

<400> SEQUENCE: 26
ttgaagtccc agtcgaacaa cgtcgaggaa ggtgactgcc aa                          42

<210> SEQ ID NO 27
<211> LENGTH: 44

-continued

<212> TYPE: DNA
<213> ORGANISM: Artificial sequence
<220> FEATURE:
<223> OTHER INFORMATION: Synthetic DNA

<400> SEQUENCE: 27
accctgaagt tcatctgcac aacgtcgagg aaggtgactg ccaa                44

<210> SEQ ID NO 28
<211> LENGTH: 43
<212> TYPE: DNA
<213> ORGANISM: Artificial sequence
<220> FEATURE:
<223> OTHER INFORMATION: Synthetic DNA

<400> SEQUENCE: 28
aagctgaccc tgaagttcca acgtcgagga aggtgactgc caa                 43

<210> SEQ ID NO 29
<211> LENGTH: 50
<212> TYPE: DNA
<213> ORGANISM: Artificial sequence
<220> FEATURE:
<223> OTHER INFORMATION: Synthetic DNA

<400> SEQUENCE: 29
aagctgaccc tgaagttcat ctgcacaacg tcgaggaagg tgactgccaa          50

<210> SEQ ID NO 30
<211> LENGTH: 40
<212> TYPE: DNA
<213> ORGANISM: Artificial sequence
<220> FEATURE:
<223> OTHER INFORMATION: Synthetic DNA

<400> SEQUENCE: 30
tgtggtagtt ggagccaacg tcgaggaagg tgactgccaa                     40

<210> SEQ ID NO 31
<211> LENGTH: 40
<212> TYPE: DNA
<213> ORGANISM: Artificial sequence
<220> FEATURE:
<223> OTHER INFORMATION: Synthetic DNA

<400> SEQUENCE: 31
gcgtaggcaa gagtgcaacg tcgaggaagg tgactgccaa                     40

<210> SEQ ID NO 32
<211> LENGTH: 31
<212> TYPE: DNA
<213> ORGANISM: Artificial sequence
<220> FEATURE:
<223> OTHER INFORMATION: Synthetic DNA

<400> SEQUENCE: 32
aagaagcaac gtcgaggaag gtgactgcca a                              31

<210> SEQ ID NO 33
<211> LENGTH: 31
<212> TYPE: DNA
<213> ORGANISM: Artificial sequence
<220> FEATURE:
<223> OTHER INFORMATION: Synthetic DNA

<400> SEQUENCE: 33
aacaaccaac gtcgaggaag gtgactgcca a    31

<210> SEQ ID NO 34
<211> LENGTH: 31
<212> TYPE: DNA
<213> ORGANISM: Artificial sequence
<220> FEATURE:
<223> OTHER INFORMATION: Synthetic DNA

<400> SEQUENCE: 34
ccaccacaac gtcgaggaag gtgactgcca a    31

<210> SEQ ID NO 35
<211> LENGTH: 31
<212> TYPE: DNA
<213> ORGANISM: Artificial sequence
<220> FEATURE:
<223> OTHER INFORMATION: Synthetic DNA

<400> SEQUENCE: 35
cctcctcaac gtcgaggaag gtgactgcca a    31

<210> SEQ ID NO 36
<211> LENGTH: 31
<212> TYPE: DNA
<213> ORGANISM: Artificial sequence
<220> FEATURE:
<223> OTHER INFORMATION: Synthetic DNA

<400> SEQUENCE: 36
ttgttgcaac gtcgaggaag gtgactgcca a    31

<210> SEQ ID NO 37
<211> LENGTH: 31
<212> TYPE: DNA
<213> ORGANISM: Artificial sequence
<220> FEATURE:
<223> OTHER INFORMATION: Synthetic DNA

<400> SEQUENCE: 37
ttcttccaac gtcgaggaag gtgactgcca a    31

<210> SEQ ID NO 38
<211> LENGTH: 31
<212> TYPE: DNA
<213> ORGANISM: Artificial sequence
<220> FEATURE:
<223> OTHER INFORMATION: Synthetic DNA

<400> SEQUENCE: 38
ggaggacaac gtcgaggaag gtgactgcca a    31

<210> SEQ ID NO 39
<211> LENGTH: 31
<212> TYPE: DNA
<213> ORGANISM: Artificial sequence
<220> FEATURE:
<223> OTHER INFORMATION: Synthetic DNA

<400> SEQUENCE: 39
ggtggtcaac gtcgaggaag gtgactgcca a    31

<210> SEQ ID NO 40
<211> LENGTH: 34
<212> TYPE: DNA
<213> ORGANISM: Artificial sequence

```
<220> FEATURE:
<223> OTHER INFORMATION: Synthetic DNA

<400> SEQUENCE: 40
gagggagagc aacgtcgagg aaggtgactg ccaa                                34

<210> SEQ ID NO 41
<211> LENGTH: 37
<212> TYPE: DNA
<213> ORGANISM: Artificial sequence
<220> FEATURE:
<223> OTHER INFORMATION: Synthetic DNA

<400> SEQUENCE: 41
ggagagggag agcaacgtcg aggaaggtga ctgccaa                             37

<210> SEQ ID NO 42
<211> LENGTH: 40
<212> TYPE: DNA
<213> ORGANISM: Artificial sequence
<220> FEATURE:
<223> OTHER INFORMATION: Synthetic DNA

<400> SEQUENCE: 42
gagggagagg gagagcaacg tcgaggaagg tgactgccaa                          40

<210> SEQ ID NO 43
<211> LENGTH: 43
<212> TYPE: DNA
<213> ORGANISM: Artificial sequence
<220> FEATURE:
<223> OTHER INFORMATION: Synthetic DNA

<400> SEQUENCE: 43
ggagagggag agggagagca acgtcgagga aggtgactgc caa                      43

<210> SEQ ID NO 44
<211> LENGTH: 46
<212> TYPE: DNA
<213> ORGANISM: Artificial sequence
<220> FEATURE:
<223> OTHER INFORMATION: Synthetic DNA

<400> SEQUENCE: 44
gagggagagg gagagggaga gcaacgtcga ggaaggtgac tgccaa                   46

<210> SEQ ID NO 45
<211> LENGTH: 21
<212> TYPE: RNA
<213> ORGANISM: Artificial sequence
<220> FEATURE:
<223> OTHER INFORMATION: Synthetic RNA

<400> SEQUENCE: 45
gagcuacagu gcuucaucuc a                                              21

<210> SEQ ID NO 46
<211> LENGTH: 21
<212> TYPE: RNA
<213> ORGANISM: Artificial sequence
<220> FEATURE:
<223> OTHER INFORMATION: Synthetic RNA

<400> SEQUENCE: 46
gagguacagu gcuucaucuc a                                              21
```

<210> SEQ ID NO 47
<211> LENGTH: 37
<212> TYPE: RNA
<213> ORGANISM: Artificial sequence
<220> FEATURE:
<223> OTHER INFORMATION: Synthetic RNA

<400> SEQUENCE: 47
gcguaggcgu uggagcgagg uacagugcuu caucuca                37

<210> SEQ ID NO 48
<211> LENGTH: 30
<212> TYPE: RNA
<213> ORGANISM: Artificial sequence
<220> FEATURE:
<223> OTHER INFORMATION: Synthetic RNA

<400> SEQUENCE: 48
cguuggagcg agguacagug cuucaucuca                30

<210> SEQ ID NO 49
<211> LENGTH: 31
<212> TYPE: RNA
<213> ORGANISM: Artificial sequence
<220> FEATURE:
<223> OTHER INFORMATION: Synthetic RNA

<400> SEQUENCE: 49
gcguuggagc gagguacagu gcuucaucuc a               31

<210> SEQ ID NO 50
<211> LENGTH: 32
<212> TYPE: RNA
<213> ORGANISM: Artificial sequence
<220> FEATURE:
<223> OTHER INFORMATION: Synthetic RNA

<400> SEQUENCE: 50
ggcguuggag cgagguacag ugcuucaucu ca              32

<210> SEQ ID NO 51
<211> LENGTH: 33
<212> TYPE: RNA
<213> ORGANISM: Artificial sequence
<220> FEATURE:
<223> OTHER INFORMATION: Synthetic RNA

<400> SEQUENCE: 51
aggcguugga gcgagguaca gugcuucauc uca             33

<210> SEQ ID NO 52
<211> LENGTH: 34
<212> TYPE: RNA
<213> ORGANISM: Artificial sequence
<220> FEATURE:
<223> OTHER INFORMATION: Synthetic RNA

<400> SEQUENCE: 52
uaggcguugg agcgagguac agugcuucau cuca            34

<210> SEQ ID NO 53
<211> LENGTH: 35
<212> TYPE: RNA
<213> ORGANISM: Artificial sequence
<220> FEATURE:
<223> OTHER INFORMATION: Synthetic RNA -continued

<400> SEQUENCE: 53
guaggcguug gagcgaggua cagugcuuca ucuca                                      35

<210> SEQ ID NO 54
<211> LENGTH: 36
<212> TYPE: RNA
<213> ORGANISM: Artificial sequence
<220> FEATURE:
<223> OTHER INFORMATION: Synthetic RNA

<400> SEQUENCE: 54
cguaggcguu ggagcgaggu acagugcuuc aucuca                                     36

<210> SEQ ID NO 55
<211> LENGTH: 39
<212> TYPE: RNA
<213> ORGANISM: Artificial sequence
<220> FEATURE:
<223> OTHER INFORMATION: Synthetic RNA

<400> SEQUENCE: 55
gggcguaggc guuggagcga gguacagugc uucaucuca                                  39

<210> SEQ ID NO 56
<211> LENGTH: 41
<212> TYPE: RNA
<213> ORGANISM: Artificial sequence
<220> FEATURE:
<223> OTHER INFORMATION: Synthetic RNA

<400> SEQUENCE: 56
gagggcguag gcguuggagc gagguacagu gcuucaucuc a                               41

<210> SEQ ID NO 57
<211> LENGTH: 45
<212> TYPE: RNA
<213> ORGANISM: Artificial sequence
<220> FEATURE:
<223> OTHER INFORMATION: Synthetic RNA

<400> SEQUENCE: 57
gagagagggc guaggcguug gagcgaggua cagugcuuca ucuca                           45

<210> SEQ ID NO 58
<211> LENGTH: 37
<212> TYPE: DNA
<213> ORGANISM: Artificial sequence
<220> FEATURE:
<221> NAME/KEY: RNA
<222> LOCATION: (1)..(16)
<223> OTHER INFORMATION: Synthetic DNA RNA chimera

<400> SEQUENCE: 58
gcguaggcgu uggagcgagg tacagtgctt catctca                                    37

<210> SEQ ID NO 59
<211> LENGTH: 37
<212> TYPE: DNA
<213> ORGANISM: Artificial sequence
<220> FEATURE:
<221> NAME/KEY: RNA
<222> LOCATION: (17)..(37)
<223> OTHER INFORMATION: Synthetic DNA RNA chimera

<400> SEQUENCE: 59
gcgtaggcgt tggagcgagg uacagugcuu caucuca        37

<210> SEQ ID NO 60
<211> LENGTH: 37
<212> TYPE: DNA
<213> ORGANISM: Artificial sequence
<220> FEATURE:
<223> OTHER INFORMATION: Synthetic DNA

<400> SEQUENCE: 60
gaggtacagt gcttcatctc agcgtaggcg ttggagc        37

<210> SEQ ID NO 61
<211> LENGTH: 30
<212> TYPE: RNA
<213> ORGANISM: Artificial sequence
<220> FEATURE:
<223> OTHER INFORMATION: Synthetic RNA

<400> SEQUENCE: 61
gagguacagu gcuucaucuc acguuggagc        30

<210> SEQ ID NO 62
<211> LENGTH: 62
<212> TYPE: DNA
<213> ORGANISM: Artificial sequence
<220> FEATURE:
<223> OTHER INFORMATION: Synthetic DNA

<400> SEQUENCE: 62
gagggagagc tttatgcgaa gcataaagga gggagagcaa cgtcgaggaa ggtgactgcc        60
aa        62

<210> SEQ ID NO 63
<211> LENGTH: 62
<212> TYPE: DNA
<213> ORGANISM: Artificial sequence
<220> FEATURE:
<223> OTHER INFORMATION: Synthetic DNA

<400> SEQUENCE: 63
gagggagagc tttatgcgaa gcataaagac acaaacacaa cgtcgaggaa ggtgactgcc        60
aa        62

<210> SEQ ID NO 64
<211> LENGTH: 62
<212> TYPE: DNA
<213> ORGANISM: Artificial sequence
<220> FEATURE:
<223> OTHER INFORMATION: Synthetic DNA

<400> SEQUENCE: 64
acacaaacac tttatgcgaa gcataaagga gggagagcaa cgtcgaggaa ggtgactgcc        60
aa        62

<210> SEQ ID NO 65
<211> LENGTH: 62
<212> TYPE: DNA
<213> ORGANISM: Artificial sequence
<220> FEATURE:
<223> OTHER INFORMATION: Synthetic DNA

<400> SEQUENCE: 65
acacaaacac tttatgcgaa gcataaagac acaaacacaa cgtcgaggaa ggtgactgcc        60

```
aa                                                                         62

<210> SEQ ID NO 66
<211> LENGTH: 40
<212> TYPE: DNA
<213> ORGANISM: Artificial sequence
<220> FEATURE:
<223> OTHER INFORMATION: Synthetic DNA

<400> SEQUENCE: 66
ggggaggtgg gagagcaacg tcgaggaagg tgactgccaa                                40

<210> SEQ ID NO 67
<211> LENGTH: 55
<212> TYPE: DNA
<213> ORGANISM: Artificial sequence
<220> FEATURE:
<223> OTHER INFORMATION: Synthetic DNA

<400> SEQUENCE: 67
ggggaggtgg gagaggaggg agagggagag caacgtcgag gaaggtgact gccaa               55

<210> SEQ ID NO 68
<211> LENGTH: 55
<212> TYPE: DNA
<213> ORGANISM: Artificial sequence
<220> FEATURE:
<223> OTHER INFORMATION: Synthetic DNA

<400> SEQUENCE: 68
ggggaggtgg gagagtattt atatttatat caacgtcgag gaaggtgact gccaa               55

<210> SEQ ID NO 69
<211> LENGTH: 63
<212> TYPE: DNA
<213> ORGANISM: Artificial sequence
<220> FEATURE:
<223> OTHER INFORMATION: Synthetic DNA

<400> SEQUENCE: 69
tactaggggg agtactgggg gagtactggg ggtagtatca acgtcgagga aggtgactgc         60
caa                                                                        63

<210> SEQ ID NO 70
<211> LENGTH: 63
<212> TYPE: DNA
<213> ORGANISM: Artificial sequence
<220> FEATURE:
<223> OTHER INFORMATION: Synthetic DNA

<400> SEQUENCE: 70
tactaggggg agtacttata tagtactggg ggtagtatca acgtcgagga aggtgactgc         60
caa                                                                        63

<210> SEQ ID NO 71
<211> LENGTH: 52
<212> TYPE: DNA
<213> ORGANISM: Artificial sequence
<220> FEATURE:
<223> OTHER INFORMATION: Synthetic DNA

<400> SEQUENCE: 71
taagtactgg gggggggggag tacttatcaa cgtcgaggaa ggtgactgcc aa                 52
```

<210> SEQ ID NO 72
<211> LENGTH: 40
<212> TYPE: DNA
<213> ORGANISM: Artificial sequence
<220> FEATURE:
<223> OTHER INFORMATION: Synthetic DNA

<400> SEQUENCE: 72
ggttggtgtg gttggcaacg tcgaggaagg tgactgccaa          40

<210> SEQ ID NO 73
<211> LENGTH: 44
<212> TYPE: DNA
<213> ORGANISM: Artificial sequence
<220> FEATURE:
<223> OTHER INFORMATION: Synthetic DNA

<400> SEQUENCE: 73
gggttgggtg tgggttgggc aacgtcgagg aaggtgactg ccaa      44

<210> SEQ ID NO 74
<211> LENGTH: 48
<212> TYPE: DNA
<213> ORGANISM: Artificial sequence
<220> FEATURE:
<223> OTHER INFORMATION: Synthetic DNA

<400> SEQUENCE: 74
ggggttgggg tgtggggttg gggcaacgtc gaggaaggtg actgccaa  48

<210> SEQ ID NO 75
<211> LENGTH: 52
<212> TYPE: DNA
<213> ORGANISM: Artificial sequence
<220> FEATURE:
<223> OTHER INFORMATION: Synthetic DNA

<400> SEQUENCE: 75
gggggttggg ggtgtggggg ttgggggcaa cgtcgaggaa ggtgactgcc aa    52

<210> SEQ ID NO 76
<211> LENGTH: 47
<212> TYPE: DNA
<213> ORGANISM: Artificial sequence
<220> FEATURE:
<223> OTHER INFORMATION: Synthetic DNA

<400> SEQUENCE: 76
gggttgggtg tgggttgggt ttcaacgtcg aggaaggtga ctgccaa   47

<210> SEQ ID NO 77
<211> LENGTH: 50
<212> TYPE: DNA
<213> ORGANISM: Artificial sequence
<220> FEATURE:
<223> OTHER INFORMATION: Synthetic DNA

<400> SEQUENCE: 77
gggttgggtg tgggttgggt tttttcaacg tcgaggaagg tgactgccaa    50

<210> SEQ ID NO 78
<211> LENGTH: 53
<212> TYPE: DNA
<213> ORGANISM: Artificial sequence
<220> FEATURE:
<223> OTHER INFORMATION: Synthetic DNA

```
<400> SEQUENCE: 78
gggttgggtg tgggttgggt ttttttttca acgtcgagga aggtgactgc caa        53

<210> SEQ ID NO 79
<211> LENGTH: 30
<212> TYPE: RNA
<213> ORGANISM: Artificial sequence
<220> FEATURE:
<223> OTHER INFORMATION: Synthetic RNA

<400> SEQUENCE: 79
ggagacaacg ucgaggaagg ugacugccaa                                   30

<210> SEQ ID NO 80
<211> LENGTH: 25
<212> TYPE: RNA
<213> ORGANISM: Artificial sequence
<220> FEATURE:
<223> OTHER INFORMATION: Synthetic RNA

<400> SEQUENCE: 80
gguguacuuc gucgugcuga agaag                                        25

<210> SEQ ID NO 81
<211> LENGTH: 25
<212> TYPE: RNA
<213> ORGANISM: Artificial sequence
<220> FEATURE:
<223> OTHER INFORMATION: Synthetic RNA

<400> SEQUENCE: 81
ccacaugaag cagcacgacu ucuuc                                        25

<210> SEQ ID NO 82
<211> LENGTH: 25
<212> TYPE: DNA
<213> ORGANISM: Artificial sequence
<220> FEATURE:
<223> OTHER INFORMATION: Synthetic DNA

<400> SEQUENCE: 82
ccacatcaag cagcacgact tcttc                                        25

<210> SEQ ID NO 83
<211> LENGTH: 37
<212> TYPE: DNA
<213> ORGANISM: Artificial sequence
<220> FEATURE:
<223> OTHER INFORMATION: Synthetic DNA

<400> SEQUENCE: 83
ggagagggag agccacatca agcagcacga cttcttc                           37

<210> SEQ ID NO 84
<211> LENGTH: 15
<212> TYPE: DNA
<213> ORGANISM: Artificial sequence
<220> FEATURE:
<223> OTHER INFORMATION: Synthetic DNA

<400> SEQUENCE: 84
ggttggtgtg gttgg                                                   15

<210> SEQ ID NO 85
```

```
<210> SEQ ID NO 85
<211> LENGTH: 20
<212> TYPE: DNA
<213> ORGANISM: Artificial sequence
<220> FEATURE:
<223> OTHER INFORMATION: Primer

<400> SEQUENCE: 85
tcactgtgcc tggaccatag                                              20

<210> SEQ ID NO 86
<211> LENGTH: 20
<212> TYPE: DNA
<213> ORGANISM: Artificial sequence
<220> FEATURE:
<223> OTHER INFORMATION: Primer

<400> SEQUENCE: 86
cagcatctgc tggttgaaga                                              20

<210> SEQ ID NO 87
<211> LENGTH: 20
<212> TYPE: DNA
<213> ORGANISM: Artificial sequence
<220> FEATURE:
<223> OTHER INFORMATION: Primer

<400> SEQUENCE: 87
gcagaagagg actggacctg                                              20

<210> SEQ ID NO 88
<211> LENGTH: 20
<212> TYPE: DNA
<213> ORGANISM: Artificial sequence
<220> FEATURE:
<223> OTHER INFORMATION: Primer

<400> SEQUENCE: 88
tagaaggcca ggagtcagga                                              20

<210> SEQ ID NO 89
<211> LENGTH: 22
<212> TYPE: DNA
<213> ORGANISM: Artificial sequence
<220> FEATURE:
<223> OTHER INFORMATION: Primer

<400> SEQUENCE: 89
gctctactga ggtgctatgt tc                                           22

<210> SEQ ID NO 90
<211> LENGTH: 21
<212> TYPE: DNA
<213> ORGANISM: Artificial sequence
<220> FEATURE:
<223> OTHER INFORMATION: Primer

<400> SEQUENCE: 90
cccttggaag atgggaaagg t                                            21

<210> SEQ ID NO 91
<211> LENGTH: 18
<212> TYPE: DNA
<213> ORGANISM: Artificial sequence
<220> FEATURE:
<223> OTHER INFORMATION: Primer

<400> SEQUENCE: 91
```

```
tcccatcacc atcttcca                                                  18

<210> SEQ ID NO 92
<211> LENGTH: 18
<212> TYPE: DNA
<213> ORGANISM: Artificial sequence
<220> FEATURE:
<223> OTHER INFORMATION: Primer

<400> SEQUENCE: 92
catcacgcca cagtttcc                                                  18

<210> SEQ ID NO 93
<211> LENGTH: 13
<212> TYPE: DNA
<213> ORGANISM: Artificial sequence
<220> FEATURE:
<223> OTHER INFORMATION: Synthetic DNA

<400> SEQUENCE: 93
gggaggggag gga                                                       13

<210> SEQ ID NO 94
<211> LENGTH: 13
<212> TYPE: DNA
<213> ORGANISM: Artificial sequence
<220> FEATURE:
<223> OTHER INFORMATION: Synthetic DNA

<400> SEQUENCE: 94
agggagggga ggg                                                       13

<210> SEQ ID NO 95
<211> LENGTH: 13
<212> TYPE: DNA
<213> ORGANISM: Artificial sequence
<220> FEATURE:
<223> OTHER INFORMATION: Synthetic DNA

<400> SEQUENCE: 95
ccctcccctc cct                                                       13
```